United States Patent
Gupta et al.

(10) Patent No.: US 9,652,362 B2
(45) Date of Patent: *May 16, 2017

(54) METHODS AND SYSTEMS OF USING APPLICATION-SPECIFIC AND APPLICATION-TYPE-SPECIFIC MODELS FOR THE EFFICIENT CLASSIFICATION OF MOBILE DEVICE BEHAVIORS

(71) Applicant: QUALCOMM Incorporated, San Diego, CA (US)

(72) Inventors: Rajarshi Gupta, Sunnyvale, CA (US); Alexander Gantman, San Diego, CA (US); Vinay Sridhara, Santa Clara, CA (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/259,501

(22) Filed: Apr. 23, 2014

(65) Prior Publication Data

US 2015/0161386 A1 Jun. 11, 2015

Related U.S. Application Data

(60) Provisional application No. 61/912,624, filed on Dec. 6, 2013.

(51) Int. Cl.
*G06F 11/00* (2006.01)
*G06F 11/36* (2006.01)
(Continued)

(52) U.S. Cl.
CPC ........ *G06F 11/3612* (2013.01); *G06F 19/707* (2013.01); *G06F 21/44* (2013.01);
(Continued)

(58) Field of Classification Search
CPC ............ H04L 63/1416; H04L 63/1408; H04L 63/145; H04L 63/1441; H04L 41/147;
(Continued)

(56) References Cited

U.S. PATENT DOCUMENTS 7,690,581 B2 *  4/2010  Takei ............... G06K 19/06056
                                                      235/462.01
7,890,581 B2 *  2/2011  Rao et al. ..................... 709/204
(Continued)

FOREIGN PATENT DOCUMENTS

CN          103533546 A       1/2014

OTHER PUBLICATIONS

Mahinthan Chandramohan, A Scalable Approach for Melware Detection through Bounded Feautre Space Behavior Modeling, 2013, IEEE, pp. 312-322.*

(Continued)

*Primary Examiner* — Ali Abyaneh
*Assistant Examiner* — Shaqueal Wade
(74) *Attorney, Agent, or Firm* — The Marbury Law Group, PLLC

(57) ABSTRACT

Methods, and mobile devices implementing the methods, use application-specific and/or application-type specific classifier to improve the efficiency and performance of a comprehensive behavioral monitoring and analysis system predicting whether a software application is causing undesirable or performance depredating behavior. The application-specific and application-type specific classifier models may include a reduced and more focused subset of the decision nodes that are included in a full or more complete classifier model that may be received or generated in the mobile device. The locally generated application-specific and/or application-type specific classifier models may be used to perform real-time behavior monitoring and analysis (Continued)

operations by applying the application-based classifier models to a behavior/feature vector generated by monitoring mobile device behavior. The various aspects focus monitoring and analysis operations on a small number of features that are most important for determining whether operations of a software application are contributing to undesirable or performance depredating behavior.

16 Claims, 14 Drawing Sheets

(51) Int. Cl.
| | |
|---|---|
| H04L 29/06 | (2006.01) |
| G06N 5/04 | (2006.01) |
| G06F 21/55 | (2013.01) |
| G06F 21/56 | (2013.01) |
| G06F 21/44 | (2013.01) |
| G06F 21/52 | (2013.01) |
| G06N 99/00 | (2010.01) |
| G06F 19/00 | (2011.01) |

(52) U.S. Cl.
CPC ............ *G06F 21/52* (2013.01); *G06F 21/552* (2013.01); *G06F 21/562* (2013.01); *G06F 21/566* (2013.01); *G06N 5/04* (2013.01); *G06N 5/043* (2013.01); *G06N 99/005* (2013.01); *H04L 63/14* (2013.01); *G06F 2221/034* (2013.01)

(58) Field of Classification Search
CPC ...... H04L 65/1063; H04L 65/00; H04W 4/00; H04W 4/12; H04W 4/14; H04W 4/02; H04W 4/16
See application file for complete search history.

(56) References Cited

U.S. PATENT DOCUMENTS

| | | | |
|---|---|---|---|
| 8,245,295 B2 | 8/2012 | Park et al. | |
| 8,266,698 B1* | 9/2012 | Seshardi | G06F 21/53 726/22 |
| 8,370,931 B1* | 2/2013 | Chien | G06F 11/3072 709/224 |
| 9,171,253 B1 | 10/2015 | Wright et al. | |
| 9,225,740 B1 | 12/2015 | Ismael et al. | |
| 2006/0085854 A1 | 4/2006 | Agrawal et al. | |
| 2007/0294271 A1 | 12/2007 | Bammi et al. | |
| 2009/0222697 A1* | 9/2009 | Thakkar | G06F 11/3676 714/38.1 |
| 2010/0192222 A1 | 7/2010 | Stokes et al. | |
| 2010/0281248 A1 | 11/2010 | Lockhart et al. | |
| 2011/0145920 A1 | 6/2011 | Mahaffey et al. | |
| 2011/0173453 A1 | 7/2011 | Parsell et al. | |
| 2011/0173693 A1 | 7/2011 | Wysopal et al. | |
| 2012/0137367 A1 | 5/2012 | Dupont et al. | |
| 2012/0210423 A1 | 8/2012 | Friedrichs et al. | |
| 2012/0311708 A1 | 12/2012 | Agarwal et al. | |
| 2013/0097706 A1 | 4/2013 | Titonis et al. | |
| 2013/0139261 A1 | 5/2013 | Friedrichs et al. | |
| 2013/0185797 A1 | 7/2013 | Zhou et al. | |
| 2013/0198565 A1 | 8/2013 | Mancoridis et al. | |
| 2013/0247187 A1 | 9/2013 | Hsiao et al. | |
| 2013/0304676 A1 | 11/2013 | Gupta et al. | |
| 2013/0305359 A1 | 11/2013 | Gathala et al. | |
| 2014/0137239 A1 | 5/2014 | Baluda et al. | |
| 2014/0188781 A1* | 7/2014 | Fawaz | G06N 5/043 706/59 |
| 2014/0241638 A1* | 8/2014 | Majumder | G06K 9/00979 382/224 |
| 2015/0161024 A1 | 6/2015 | Gupta et al. | |

OTHER PUBLICATIONS

Burguera I., et al., "Crowdroid", Security and Privacy in Smartphones and Mobile Devices, ACM, 2 Penn Plaza, Suite 701, New York NY 10121-0701 USA, Oct. 17, 2011, XP058005976, DOI: 10.1145/2046614.2046619 ISBN: 978-1-4503-1000-0, pp. 15-26.

Chandramohan Mahinthan et al: "A scalable approach for malware detection through bounded feature space behavior modeling", 2013 28th IEEE/ACM International Conference on Automated Software Engineering (ASE), IEEE, Nov. 11, 2013, pp. 312-322, XP032546944, DOI: 10. 1109/ASE.2013.6693090 [retrieved on Dec. 23, 2013].

Firdausi I et al: "Analysis of Machine learning Techniques Used in Behavior-Based Malware Detection", Advances in Computing, Control and Telecommunication Technologies (ACT), 2010 Second International Conference on, IEEE, Piscataway, NJ, USA, Dec. 2, 2010, XP031840644, ISBN: 978-1-4244-8746-2, pp. 201-203.

International Search Report and Written Opinion—PCT/US2014/068944—ISA/EPO—Mar. 17, 2015.

Schmidt A.D., et al., "Monitoring Smartphones for Anomaly Detection", Mobile Networks and Applications, vol. 14, No. 1, Feb. 1, 2009, pp. 92-106, XP055115882, ISSN: 1383-469X, DOI:10.1007/s11036-008-0113-x.

Shamili A.S., et al., "Malware detection on mobile devices using distributed machine learning", Proceedings of the 20th International Conference on Pattern Recognition (ICPR'10), Aug. 23, 2010 (Aug. 23, 2010), pp. 4348-4351, XP031772702, DOI: 10.1109/ICPR.2010.1057 the whole document.

Shabtai A., "Malware Detection on Mobile Devices," Eleventh International Conference on Mobile Data Management, IEEE Computer Society, 2010, pp. 289-290.

* cited by examiner

METHODS AND SYSTEMS OF USING APPLICATION-SPECIFIC AND APPLICATION-TYPE-SPECIFIC MODELS FOR THE EFFICIENT CLASSIFICATION OF MOBILE DEVICE BEHAVIORS

RELATED APPLICATIONS

This application claims the benefit of priority to U.S. Provisional Application No. 61/912,624 entitled "Methods and Systems of Using Application-Specific and Application-Type-Specific Models for the Efficient Classification of Mobile Device Behaviors" filed Dec. 6, 2013, the entire contents of which are incorporated herein by reference for all purposes.

BACKGROUND

Cellular and wireless communication technologies have seen explosive growth over the past several years. This growth has been fueled by better communications, hardware, larger networks, and more reliable protocols. As a result, wireless service providers are now able to offer their customers with unprecedented levels of access to information, resources, and communications.

To keep pace with these service enhancements, mobile electronic devices (e.g., cellular phones, tablets, laptops, etc.) have become more powerful and complex than ever. This complexity has created new opportunities for malicious software, software conflicts, hardware faults, and other similar errors or phenomena to negatively impact a mobile device's long-term and continued performance and power utilization levels. Accordingly, identifying and correcting the conditions and/or mobile device behaviors that may negatively impact the mobile device's long term and continued performance and power utilization levels is beneficial to consumers.

SUMMARY

The various aspects include methods of generating data models in a mobile device by receiving in a processor of the mobile device a full classifier model that includes a plurality of test conditions, identifying mobile device features used by a software application of the mobile device or a type of software application that may execute on the mobile device, identifying test conditions in the plurality of test conditions that evaluate the identified mobile device features, generating an application-based classifier model that prioritizes the identified test conditions (the application-based classifier model being an application-specific classifier model or an application-type-specific classifier model) and using the generated application-based classifier model in the mobile device to classify a behavior of the mobile device.

In an aspect, identifying mobile device features may include identifying mobile device features used by the software application, and generating the application-based classifier model may include generating the application-specific classifier model. In a further aspect, identifying mobile device features may include identifying mobile device features used by one type of software application that may execute on the mobile device, and generating the application-based classifier model may include generating the application-type-specific classifier model.

In a further aspect, the method may include monitoring the behavior over a period of time by collecting behavior information from a mobile device component. In a further aspect, using the application-based classifier model in the mobile device to classify the behavior of the mobile device may include using the behavior information to generate a feature vector, evaluating each test condition included in the application-based classifier model by applying the generated feature vector to the application-based classifier model, computing a weighted average of each result of evaluating test conditions in the application-based classifier model, and determining whether the behavior is malicious or benign based on the weighted average.

In a further aspect, receiving the full classifier model that identifies the plurality of test conditions may include receiving a finite state machine that may include information that is suitable for conversion into a plurality of decision nodes that each evaluates one of the plurality of test conditions. In an aspect, generating the application-based classifier model that prioritizes the identified test conditions may include generating the application-based classifier model to include decision nodes that evaluate one of a mobile device feature that is relevant to the software application and/or a mobile device feature that is relevant to the type of software application.

In a further aspect, generating the application-based classifier model that prioritizes the identified test conditions may include determining a number of unique test conditions that should be evaluated to classify the behavior without consuming an excessive amount of mobile device resources (e.g., memory, processing, and battery resources), generating a list of test conditions by sequentially traversing the plurality of test conditions in the full classifier model and inserting those test conditions that are relevant to features that may be accessed and used by the software application into the list of test conditions until the list of test conditions includes the determined number of unique test conditions, and generating the application-based classifier model to include the decision nodes that are included in the full classifier model and test one of the test conditions included in the generated list of test conditions.

In a further aspect, receiving the full classifier model that identifies the plurality of test conditions may include receiving a finite state machine. In an further aspect, the method include converting the finite state machine into boosted decision stumps that each evaluate one of the plurality of test conditions, generating a family of lean classifier models in the mobile device based on the boosted decision stumps, selecting a lean classifier models from the family of lean classifier models, and applying collected behavior information to the application-based classifier model and the selected lean classifier model in parallel.

In a further aspect, identifying mobile device features may include identifying mobile device features used by the software application. In a further aspect, the method may include monitoring the software application to detect a change in one of a state of the software application, a configuration of the software application, an operation of the software application, and a functionality of the software application. In a further aspect, the method may include modifying the application-based classifier model to include an updated set of test conditions in response to detecting the change, and using the modified application-based classifier model to reclassify the behavior of the mobile device.

In a further aspect, monitoring the software application and modifying the application-based classifier model to include the updated set of test conditions in response to detecting the change may include identifying a feature associated with the detected change, determining whether the identified feature is included in the application-based classifier model, identifying a test condition in the plurality of test conditions that evaluate the identified feature, and adding the identified test condition to the application-based classifier model in response to determining that the identified feature is not included in the application-based classifier model. In a further aspect, the method may include generating the full classifier model in a server by receiving in the server a corpus of behavior information, generating a finite state machine based on the corpus of behavior information to include data that is suitable for conversion into a plurality of boosted decision stumps, and sending the finite state machine to the mobile device as the full classifier model.

Further aspects include a mobile computing device having a processor configured with processor-executable instructions to perform operations that may include receiving a full classifier model that includes a plurality of test conditions, identifying mobile device features used by one of a software application of the mobile computing device and a type of software application that may execute on the mobile computing device, identifying test conditions in the plurality of test conditions that evaluate the identified mobile device features, generating an application-based classifier model (i.e., an application-specific classifier model or an application-type-specific classifier model) that prioritizes the identified test conditions, and using the generated application-based classifier model to classify a behavior of the mobile computing device.

In an aspect, the processor may be configured with processor-executable instructions to perform operations such that identifying mobile device features may include identifying mobile device features used by the software application, and generating the application-based classifier model may include generating the application-specific classifier model. In a further aspect, the processor may be configured with processor-executable instructions to perform operations such that identifying mobile device features may include identifying mobile device features used by one type of software application that may execute on the mobile computing device, and generating the application-based classifier model may include generating the application-type-specific classifier model.

In a further aspect, the processor may be configured with processor-executable instructions to perform operations that further include monitoring the behavior over a period of time by collecting behavior information from a mobile device component. In a further aspect, the processor may be configured with processor-executable instructions to perform operations such that using the application-based classifier model to classify the behavior may include using the behavior information to generate a feature vector, evaluating each test condition included in the application-based classifier model by applying the generated feature vector to the application-based classifier model, computing a weighted average of each result of evaluating test conditions in the application-based classifier model, and determining whether the behavior is malicious or benign based on the weighted average.

In a further aspect, the processor may be configured with processor-executable instructions to perform operations such that receiving the full classifier model that identifies the plurality of test conditions may include receiving a finite state machine that includes information that is suitable for conversion into a plurality of decision nodes that each evaluate one of the plurality of test conditions, and generating the application-based classifier model that prioritizes the identified test conditions may include generating the application-based classifier model to include decision nodes that evaluate one of a mobile device feature that is relevant to the software application, and a mobile device feature that is relevant to the type of software application.

In a further aspect, the processor may be configured with processor-executable instructions to perform operations such that generating the application-based classifier model that prioritizes the identified test conditions may further include determining a number of unique test conditions that should be evaluated to classify the behavior without consuming an excessive amount of mobile device resources, generating a list of test conditions by sequentially traversing the plurality of test conditions in the full classifier model and inserting those test conditions that are relevant to features that may be accessed and used by the software application into the list of test conditions until the list of test conditions includes the number of unique test conditions, and generating the application-based classifier model to include the decision nodes in the full classifier model that test one of the test conditions included in the generated list of test conditions.

Further aspects include a non-transitory computer readable storage medium having stored thereon processor-executable software instructions configured to cause a processor to perform operations that include receiving a full classifier model that includes a plurality of test conditions, identifying mobile device features used by one of a software application and a type of software application that may execute on the mobile device, identifying test conditions in the plurality of test conditions that evaluate the identified mobile device features, generating an application-based classifier model (e.g., an application-specific classifier model or an application-type-specific classifier model) that prioritizes the identified test conditions, and using the generated application-based classifier model to classify a behavior of the mobile device.

In an aspect, the stored processor-executable software instructions may be configured to cause a processor to perform operations such that identifying mobile device features may include identifying mobile device features used by the software application, and generating the application-based classifier model may include generating the application-specific classifier model. In a further aspect, the stored processor-executable software instructions may be configured to cause a processor to perform operations such that identifying mobile device features may include identifying mobile device features used by one type of software application that may execute on the mobile device, and generating the application-based classifier model may include generating the application-type-specific classifier model.

In a further aspect, the stored processor-executable software instructions may be configured to cause a processor to perform operations that further include monitoring the behavior over a period of time by collecting behavior information from a mobile device component. In a further aspect, the stored processor-executable software instructions may be configured to cause a processor to perform operations such that using the application-based classifier model to classify the behavior of the mobile device may include using the behavior information to generate a feature vector, evaluating each test condition included in the application-based classifier model by applying the generated feature vector to the application-based classifier model, computing a weighted average of each result of evaluating test conditions in the application-based classifier model, and determining whether the behavior is malicious or benign based on the weighted average.

In a further aspect, the stored processor-executable software instructions may be configured to cause a processor to perform operations such that receiving the full classifier model that identifies the plurality of test conditions may include receiving a finite state machine that includes information that is suitable for conversion into a plurality of decision nodes that each evaluate one of the plurality of test conditions, and generating the application-based classifier model that prioritizes the identified test conditions may include generating the application-based classifier model to include decision nodes that evaluate a mobile device feature that is relevant to the software application or to the type of software application.

In a further aspect, the stored processor-executable software instructions may be configured to cause a processor to perform operations such that generating the application-based classifier model that prioritizes the identified test conditions may further include determining a number of unique test conditions that should be evaluated to classify the behavior without consuming an excessive amount of mobile device resources, generating a list of test conditions by sequentially traversing the plurality of test conditions in the full classifier model, and inserting those test conditions that are relevant to features that may be accessed and used by the software application into the list of test conditions until the list of test conditions includes the number of unique test conditions, and generating the application-based classifier model to include the decision nodes in the full classifier model that test one of the test conditions included in the generated list of test conditions.

Further aspects include a computing device that may include means for receiving a full classifier model that includes a plurality of test conditions, means for identifying mobile device features used by a software application or a type of software application that may execute on the mobile computing device, means for identifying test conditions in the plurality of test conditions that evaluate the identified mobile device features, means for generating an application-based classifier model that prioritizes the identified test conditions, and means for using the generated application-based classifier model to classify a behavior of the mobile computing device.

In an aspect, means for identifying mobile device features may include means for identifying mobile device features used by the software application. In a further aspect, means for generating the application-based classifier model may include means for generating the application-specific classifier model. In an aspect, means for identifying mobile device features may include means for identifying mobile device features used by one type of software application that may execute on the mobile computing device, and means for generating the application-based classifier model may include generating the application-type-specific classifier model.

In a further aspect, the computing device may include means for monitoring the behavior over a period of time by collecting behavior information from a mobile device component. In a further aspect, means for using the application-based classifier model to classify the behavior of the mobile computing device may include means for using the behavior information to generate a feature vector, means for evaluating each test condition included in the application-based classifier model by applying the generated feature vector to the application-based classifier model, means for computing a weighted average of each result of evaluating test conditions in the application-based classifier model, and means for determining whether the behavior is malicious or benign based on the weighted average.

In a further aspect, means for receiving the full classifier model that identifies the plurality of test conditions may include means for receiving a finite state machine that includes information that is suitable for conversion into a plurality of decision nodes that each evaluate one of the plurality of test conditions, and means for generating the application-based classifier model that prioritizes the identified test conditions may include means for generating the application-based classifier model to include decision nodes that evaluate a mobile device feature that is relevant to the software application or a mobile device feature that is relevant to the type of software application.

In a further aspect, means for generating the application-based classifier model that prioritizes the identified test conditions further may include means for determining a number of unique test conditions that should be evaluated to classify the behavior without consuming an excessive amount of mobile device resources, means for generating a list of test conditions by sequentially traversing the plurality of test conditions in the full classifier model and inserting those test conditions that are relevant to features that may be accessed and used by the software application into the list of test conditions until the list of test conditions includes the number of unique test conditions, and means for generating the application-based classifier model to include the decision nodes in the full classifier model that test one of the test conditions included in the generated list of test conditions.

In a further aspect, means for receiving the full classifier model that identifies the plurality of test conditions may include means for receiving a finite state machine. In a further aspect, the mobile computing device may further include means for converting the finite state machine into boosted decision stumps that each evaluate one of the plurality of test conditions, means for generating a family of lean classifier models based on the boosted decision stumps, means for selecting a lean classifier models from the family of lean classifier models, and means for applying collected behavior information to the application-based classifier model and the selected lean classifier model in parallel.

In a further aspect, means for identifying mobile device features may include means for identifying mobile device features used by the software application. In a further aspect, the mobile computing device may further include means for monitoring the software application to detect a change in one of a state of the software application, a configuration of the software application, an operation of the software application, and a functionality of the software application. In a further aspect, the computing device may include means for modifying the application-based classifier model to include an updated set of test conditions in response to detecting the change, and means for using the modified application-based classifier model to reclassify the behavior.

BRIEF DESCRIPTION OF THE DRAWINGS

The accompanying drawings, which are incorporated herein and constitute part of this specification, illustrate exemplary aspects of the invention, and together with the general description given above and the detailed description given below, serve to explain the features of the invention.

DETAILED DESCRIPTION

Figure 1:
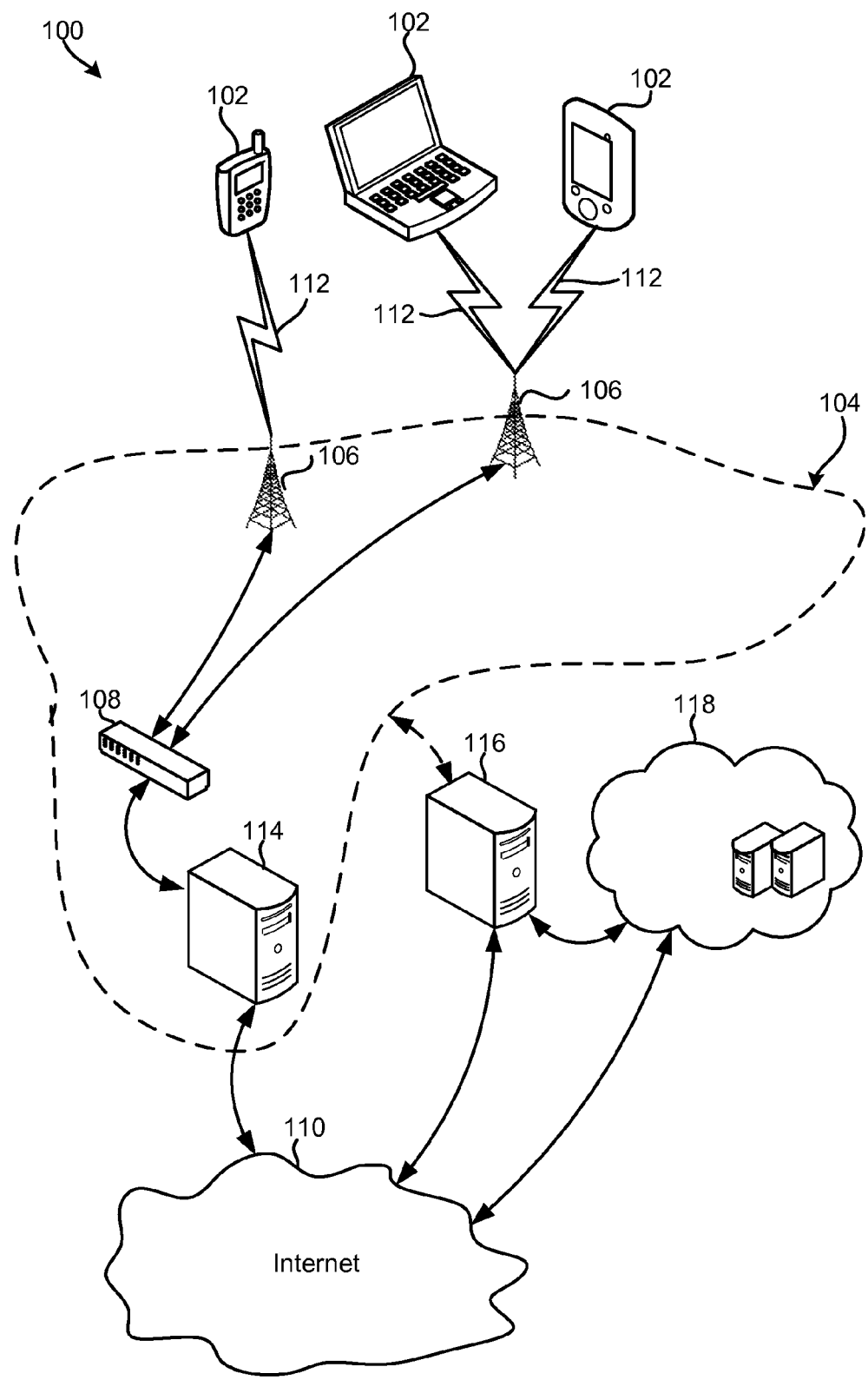
FIG. 1 is a communication system block diagram illustrating network components of an example telecommunication system that is suitable for use with the various aspects.

The various aspects will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

In overview, the various aspects include methods, and mobile devices configured to implement the methods, of using application-specific and/or application-type specific classifier models (i.e., data or behavior models) to improve the efficiency and performance of a comprehensive behavioral monitoring and analysis system, and to enable the mobile device to better predict whether a software application is a source or cause of an undesirable or performance deprecating behavior of the mobile device. For ease of reference, the term "application-based classifier models" is used herein and in the claims to refer to either or both of application-specific and application-type specific classifier models as described below.

The comprehensive behavioral monitoring and analysis system may include a network server and a mobile device configured to work in conjunction with one another to intelligently and efficiently identify, classify, model, prevent, and/or correct the conditions and/or mobile device behaviors that often degrade the mobile device's performance and/or power utilization levels over time. The network server may be configured to receive information on various conditions, features, behaviors, and corrective actions from a central database (e.g., the "cloud"), and use this information to generate a full or robust classifier model (e.g., a data/behavior model) that describes a large corpus of information (e.g., behavior information) in a format or structure that can be quickly converted into one or more lean classifier models by a mobile device. For example, the network server may generate the full classifier model to include a plurality of decision nodes (e.g., boosted decision trees, boosted decision stumps, etc.) that each evaluate or test a feature of the mobile device, and which may be included in a lean classifier model.

The network server may send the full classifier to the mobile device. The mobile device may be configured to receive and use the full classifier model to generate a lean classifier model or a family of lean classifier models of varying levels of complexity (or "leanness"). To accomplish this, the mobile device may trim, cull, or prune the decision nodes included in the full classifier model to generate lean classifier models that include a reduced number of the decision nodes and/or evaluate a limited number of test conditions.

In addition, the mobile device may also dynamically generate application-specific and/or application-type specific classifier models that identify and test conditions or features that are relevant to a specific software application (Google® wallet) and/or to a specific type of software application (e.g., games, navigation, financial, news, productivity, etc.). In an aspect, these application-based classifier models (i.e., the application-specific and application-type specific classifier models) may be generated to include a reduced and more focused subset of the decision nodes that are included in the received full classifier model or of those included in lean classifier model generated from the received full classifier model.

In various aspects, the mobile device may be configured to generate application-based classifier models for each software application in the system and/or for each type of software application in the system. The mobile device may also be configured to dynamically identify the software applications and/or application types that are a high risk or susceptible to abuse (e.g., financial applications, point-of-sale applications, biometric sensor applications, etc.), and generate application-based classifier models for only the software applications and/or application types that are identified as being high risk or susceptible to abuse. In various aspects, the mobile device may be configured to generate the application-based classifier models dynamically, reactively, proactively, and/or every time a new application is installed or updated.

The mobile device may be configured to use the locally generated lean and/or application-based classifier models to perform real-time behavior monitoring and analysis operations. In an aspect, the mobile device may be configured to use or apply multiple classifier models in parallel. In various aspects, the mobile device may be configured to give preference or priority to the results generated from using or applying the application-based classifier models to a behavior/feature vector over the results generated from using/ applying a more generic lean classifier model to the same or different behavior/feature vector when evaluating a specific software application. In the various aspects, the mobile device may use the results of applying the classifier models to predict whether a software application, process, or complex mobile device behavior is benign or contributing to the degradation of the performance or power consumption characteristics of the mobile device.

By dynamically generating classifier models locally in the mobile device so that they are focused or based on application-specific or application-type-specific features, the various aspects allow the mobile device to focus its monitoring and analysis operations on a small number of features that are most important for determining whether the operations of a specific software application are contributing to an undesirable or performance depredating behavior of the mobile device. This improves the performance and power consumption characteristics of the mobile device, and allows the mobile device to perform the real-time behavior monitoring and analysis operations continuously or near continuously without consuming an excessive amount of mobile device resources (e.g., processing, memory, or energy resources).

The word "exemplary" is used herein to mean "serving as an example, instance, or illustration." Any implementation described herein as "exemplary" is not necessarily to be construed as preferred or advantageous over other implementations.

The phrase "application-based classifier model" is used generically herein to refer to both an application-specific classifier model and an application-type-specific classifier model collectively and in the alternative. That is, an application-based classifier model may be an application-specific classifier model or an application-type-specific classifier model. An application-specific classifier model may be a classifier model that identifies or includes data, information structures (e.g., feature vectors, behavior vectors, component lists, etc.), and/or decision criteria that may be used to evaluate an individual software application. An application-type-specific classifier model may be a classifier model that identifies or includes data, information structures, and/or decision criteria that that relate to evaluating a particular class, category, or type of software application (e.g., financial applications, productivity applications, etc.).

The terms "mobile computing device" and "mobile device" are used interchangeably herein to refer to any one or all of cellular telephones, smartphones, personal or mobile multi-media players, personal data assistants (PDA's), laptop computers, tablet computers, smartbooks, ultrabooks, palm-top computers, wireless electronic mail receivers, multimedia Internet enabled cellular telephones, wireless gaming controllers, and similar personal electronic devices which include a memory, a programmable processor for which performance is important, and operate under battery power such that power conservation methods are of benefit. While the various aspects are particularly useful for mobile computing devices, such as smartphones, which have limited resources and run on battery, the aspects are generally useful in any electronic device that includes a processor and executes application programs.

Generally, the performance and power efficiency of a mobile device degrade over time. Recently, anti-virus companies (e.g., McAfee, Symantec, etc.) have begun marketing mobile anti-virus, firewall, and encryption products that aim to slow this degradation. However, many of these solutions rely on the periodic execution of a computationally-intensive scanning engine on the mobile device, which may consume many of the mobile device's processing and battery resources, slow or render the mobile device useless for extended periods of time, and/or otherwise degrade the user experience. In addition, these solutions are typically limited to detecting known viruses and malware, and do not address the multiple complex factors and/or the interactions that often combine to contribute to a mobile device's degradation over time (e.g., when the performance degradation is not caused by viruses or malware). For these and other reasons, existing anti-virus, firewall, and encryption products do not provide adequate solutions for identifying the numerous factors that may contribute to a mobile device's degradation over time, for preventing mobile device degradation, or for efficiently restoring an aging mobile device to its original condition.

Currently, various solutions exist for modeling the behavior an application program executing on a computing device, and these solutions may be used along with machine learning techniques to determine whether a software application is malicious or benign. However, these solutions are not suitable for use on mobile devices because they require evaluating a very large corpus of behavior information, do not generate behavior models dynamically to account for application-specific or application-type-specific features of the computing device, do not intelligently prioritize the features in the behavior model, are limited to evaluating an individual application program or process, and/or require the execution of computationally-intensive processes in the mobile device. As such, implementing or performing these existing solutions in a mobile device may have a significant negative and/or user-perceivable impact on the responsiveness, performance, or power consumption characteristics of the mobile device.

For example, a computing device may be configured to use an existing machine learning-based solution to access and use a large corpus of training data, derive a model that takes as input a feature vector, and use this model to determine whether a software application of the computing device is malicious or benign. However, such a solution does not generate a full classifier model (i.e., a robust data or behavior model) that describes the large corpus of behavior information in a format or information structure (e.g., finite state machine, etc.) that may be used by a mobile device to quickly generate a lean classifier model. For at least this reason, such a solution does not allow a mobile device to generate a lean classifier model that includes decision nodes that focus on or prioritize the conditions or features that are specific to an individual application or application type. In addition, this solution does not allow a mobile device to generate a lean classifier model that intelligently identifies or prioritizes the features in accordance to their relevance to classifying a specific behavior, software application, or software application type in the specific mobile device in which the model is used. For these and other reasons, such a solution cannot be used by a mobile device processor to quickly and efficiently identify, analyze, or classify a software application as contributing to a complex mobile device behavior that has significant negative or user-perceivable impact on the responsiveness, performance, or power consumption characteristics of the mobile device.

In addition to the above-mentioned limitations of existing solutions, many behavior modeling solutions implement a "one-size-fits-all" approach to modeling the behaviors of a computing device, and are therefore not suitable for use in mobile devices. That is, these solutions typically generate the behavior models so that they are generic and may be used in many computing devices and/or with a variety of different hardware and software configurations. As such, these generic behavior models often include/test a very large number of features, many of which are not relevant to (and thus cannot be used for) identifying, analyzing, or classifying a behavior of a specific software application or application type in the specific computing device in which they are actually used. In addition, these solutions do not assign relative priorities to features based their relevance to classifying a specific behavior in the specific mobile device in which the model is used. Therefore, these solutions typically require that a computing device apply behavior models that include a large number of disorganized, improperly prioritized, or irrelevant features. Such models are not suitable for use in resource-constrained mobile devices because they may cause the mobile device processor to analyze a large number of features that are not useful for identifying a cause or source of the mobile device's degradation over time. As such, these existing solutions are not suitable for use in complex-yet resource-constrained mobile devices.

Modern mobile devices are highly configurable and complex systems. As such, the features that are most important for determining whether a particular mobile device behavior is benign or not benign (e.g., malicious or performance-degrading) may be different in each mobile device. Further, a different combination of features may require monitoring and/or analysis in each mobile device in order for that mobile device to quickly and efficiently determine whether a particular behavior is benign or not benign. Yet, the precise combination of features that require monitoring and analysis, and the relative priority or importance of each feature or feature combination, can often only be determined using application-specific, application-type specific, and/or device-specific information obtained from the specific mobile device in which the behavior is to be monitored or analyzed. For these and other reasons, behavior models generated in any computing device other than the specific device in which they are used cannot include information that identifies the precise combination of features that are most important to classifying a software application or mobile device behavior in that device.

For example, if a first mobile device is configured to use its biometric sensors (e.g., fingerprint reader, voice recognition subsystem, retina scanner, etc.) to authorize financial transactions, then features that test conditions relating to the access and use of the biometric sensors are likely to be relevant in determining whether an observed behavior of accessing financial software is malicious or benign in that mobile device. For example, the access and use of the biometric sensors in the first mobile device may indicate that a malicious application is authorizing financial transactions without the user's knowledge or consent. On the other hand, features that test conditions relating to the access and use of these sensors are not likely to be relevant in determining whether the observed behavior of accessing financial software is malicious or benign in a second mobile device which is not configured to use its biometric sensors to authorize financial transactions. That is, since the first and second devices may be identical in all aspects (i.e., are the same type, model, operating system, software, etc.) except for their configuration for the use of their biometric sensors, it would be challenging to generate a generic behavior model that accurately identifies features that evaluate conditions relating to the access and use of the biometric sensors for both devices. It would be even more challenging to generate a generic model that tests much more complicated conditions or features on hundreds of thousands (or millions) of similarly equipment yet independently configurable mobile devices.

In addition, mobile devices are resource constrained systems that have relatively limited processing, memory, and energy resources. Modern mobile devices are also complex systems having a large variety of factors that may contribute to the degradation in performance and power utilization levels of the mobile device over time. Examples of factors that may contribute to performance degradation include poorly designed software applications, malware, viruses, fragmented memory, and background processes. Due to the number, variety, and complexity of these factors, it is often not feasible to evaluate all of the various components, behaviors, processes, operations, conditions, states, or features (or combinations thereof) that may degrade performance and/or power utilization levels of the complex yet resource-constrained systems of modern mobile devices. As such, it is difficult for users, operating systems, or application programs (e.g., anti-virus software, etc.) to accurately and efficiently identify the sources of such problems. As a result, mobile device users currently have few remedies for preventing the degradation in performance and power utilization levels of a mobile device over time, or for restoring an aging mobile device to its original performance and power utilization levels.

The various aspects include a comprehensive behavioral monitoring and analysis system for intelligently and efficiently identifying, preventing, and/or correcting the conditions, factors, and/or mobile device behaviors that often degrade a mobile device's performance and/or power utilization levels over time. In an aspect, an observer process, daemon, module, or sub-system (herein collectively referred to as a "module") of the mobile device may instrument or coordinate various application programming interfaces (APIs), registers, counters or other mobile device components (herein collectively "instrumented components") at various levels of the mobile device system. The observer module may continuously (or near continuously) monitor mobile device behaviors by collecting behavior information from the instrumented component. The mobile device may also include an analyzer module, and the observer module may communicate (e.g., via a memory write operation, function call, etc.) the collected behavior information to the analyzer module. The analyzer module may receive and use the behavior information to generate feature or behavior vectors, generate spatial and/or temporal correlations based on the feature/behavior vectors, and use this information to determine whether a particular mobile device behavior, condition, sub-system, software application, or process is benign, suspicious, or not benign (i.e., malicious or performance-degrading). The mobile device may then use the results of this analysis to heal, cure, isolate, or otherwise fix or respond to identified problems.

The analyzer module may also be configured to perform real-time behavior analysis operations, which may include performing, executing, and/or applying data, algorithms, classifiers or models (herein collectively referred to as "classifier models") to the collected behavior information to determine whether a software application or mobile device behavior is benign or not benign (e.g., malicious or performance-degrading). Each classifier model may be a behavior model that includes data and/or information structures (e.g., feature vectors, behavior vectors, component lists, etc.) that may be used by a mobile device processor to evaluate a specific feature or aspect of a mobile device's behavior. Each classifier model may also include decision criteria for monitoring a number of features, factors, data points, entries, APIs, states, conditions, behaviors, applications, processes, operations, components, etc. (herein collectively "features") in the mobile device. The classifier models may be preinstalled on the mobile device, downloaded or received from a network server, generated in the mobile device, or any combination thereof. The classifier models may be generated by using crowd sourcing solutions, behavior modeling techniques, machine learning algorithms, etc.

Each classifier model may be categorized as a full classifier model or a lean classifier model. A full classifier model may be a robust data model that is generated as a function of a large training dataset, which may include thousands of features and billions of entries. A lean classifier model may be a more focused data model that is generated from a reduced dataset that includes or prioritizes tests on the features/entries that are most relevant for determining whether a particular mobile device behavior is benign or not benign (e.g., malicious or performance-degrading).

A locally generated lean classifier model is a lean classifier model that is generated in the mobile device. An application-based classifier model may be an application specific classifier model or an application-type specific classifier model. An application specific classifier model is a classifier model that includes a focused data model that includes or prioritizes tests on the features/entries that are most relevant for determining whether a particular software application is benign or not benign (e.g., malicious or performance-degrading). An application-type specific classifier model is a classifier model that includes a focused or prioritized data model that includes or prioritizes tests on the features/entries that are most relevant for determining whether a particular type of software application is benign or not benign (e.g., malicious or performance-degrading).

As mentioned above, there may be thousands of features/factors and billions of data points that require analysis to properly identify the cause or source of a mobile device's degradation. Therefore, classifier models may be trained on a very large number of features in order to support all makes and models of mobile devices, and for each mobile device to make accurate decisions regarding whether a particular mobile device behavior is benign or not benign (e.g., malicious or performance-degrading). Yet, because mobile devices are resource constrained systems, it is often not feasible for the mobile device evaluate all these features. Further, mobile devices come in many different configurations and varieties, and may include a large number of different software applications or application types. Yet, few mobile devices (if any) include every feature or functionality that may be addressed in full classifier models. The various aspects generate lean application-based classifier models that the analyzer module may apply to evaluate a targeted subset of features that are most relevant to the software applications of a specific mobile device, limiting the number of test conditions and analyses that would otherwise be performed if a generic or full classifier model was used when classifying a mobile device behavior.

The various aspects include mobile devices and network servers configured to work in conjunction with one another to intelligently and efficiently identify the features, factors, and data points that are most relevant to determining whether a mobile device behavior is benign or not benign (e.g., malicious or performance-degrading). By generating lean classifier models locally in the mobile device accounting for device-specific features and/or device-state-specific features, the various aspects allow the mobile device processor to apply focused classifier models to quickly and efficiently identify, analyze, or classify a complex mobile device behavior (e.g., via the observer and analyzer modules, etc.) without causing a significant negative or user-perceivable change in the responsiveness, performance, or power consumption characteristics of the mobile device.

A full classifier model may be generated by a network server configured to receive a large amount of information regarding mobile device behaviors and states, features, and conditions during or characterizing those behaviors from a cloud service/network. This information may be in the form of a very large cloud corpus of mobile device behavior vectors. The network server may use this information to generate a full classifier model (i.e., a robust data/behavior model) that accurately describes the very large cloud corpus of behavior vectors. The network server may generate the full classifier model to include all or most of the features, data points, and/or factors that could contribute to the degradation over time of any of a number of different makes, models, and configurations of mobile devices.

In an aspect, the network server may generate the full classifier model to include a finite state machine expression or representation, which may be an information structure that includes a boosted decision tree/stump or family of boosted decision trees/stumps that can be quickly and efficiently culled, modified or converted into lean classifier models that are suitable for use or execution in a mobile device processor. The finite state machine expression or representation (abbreviated to "finite state machine") may be an information structure that includes test conditions, state information, state-transition rules, and other similar information. In an aspect, the finite state machine may be an information structure that includes a large or robust family of boosted decision stumps that each evaluate or test a feature, condition, or aspect of a mobile device behavior.

The mobile device may be configured to receive a full classifier model from the network server, and use the received full classifier model to generate lean classifier models (i.e., data/behavior models) that are specific for the features and functionalities of the mobile device.

In various aspects, the mobile device may use behavior modeling and machine learning techniques to intelligently and dynamically generate the lean classifier models so that they account for device-specific and/or device-state-specific features of the mobile device (e.g., features relevant to the mobile device configuration, functionality, connected/included hardware, etc.), include, test or evaluate a focused and targeted subset of the features that are determined to be important for identifying a cause or source of the mobile device's degradation over time, and/or prioritize the targeted subset of features based on probability or confidence values identifying their relative importance for successfully classifying a behavior in the specific mobile device in which they are used/evaluated.

By generating classifier models in the mobile device in which the models are used, the various aspects allow the mobile device to accurately identify the specific features that are most important in determining whether a behavior on that specific mobile device is benign or contributing to that device degradation in performance. These aspects also allow the mobile device to accurately prioritize the features in the lean classifier models in accordance with their relative importance to classifying behaviors in that specific mobile device.

The use of application-specific, application-type specific, device-specific and/or device-specific information allows the mobile device to quickly identify and prioritize the features that should be included in the lean classifier models, as well as to identify the features that should be excluded from the lean classifier models. For example, the mobile device may be configured to identify and exclude from the lean classifier models the features/nodes/trees/stumps included in the full model that test conditions which do not pertain to a software application running on the mobile device based on its specific feature set, and therefore are not relevant to the mobile device. For example, a mobile device that does not include a biometric sensor may exclude from lean classifier models all features/nodes/stumps that test or evaluate conditions relating to the use of a biometric sensor by a software application.

Further, since the lean classifier models include a reduced subset of states, features, behaviors, or conditions that must be evaluated (i.e., compared to the full classifier model), the observer and/or analyzer modules may use the lean classifier model to quickly and accurately determine whether a mobile device behavior is benign or not benign (e.g., malicious or performance-degrading) without consuming an excessive amount of processing, memory, or energy resources of the mobile device.

In an aspect, the mobile device may be configured to use the full classifier model to generate a family of lean classifier models of varying levels of complexity (or "leanness"). The leanest family of lean classifier models (i.e., the lean classifier model based on the fewest number of test conditions) may be applied routinely until a behavior is encountered that the model cannot categorize as either benign or malicious (and therefore is categorized by the model as suspicious), at which time a more robust (i.e., less lean) lean classifier model may be applied in an attempt to categorize the behavior as either benign or malicious. The application of ever more robust lean classifier models within the family of generated lean classifier models may be applied until a definitive classification of the behavior is achieved. In this manner, the observer and/or analyzer modules can strike a balance between efficiency and accuracy by limiting the use of the most complete, but resource-intensive lean classifier models to those situations where a robust classifier model is needed to definitively classify a behavior.

In various aspects, the mobile device may be configured to generate one or more lean classifier models by converting a finite state machine representation/expression into boosted decision stumps, pruning or culling the full set of boosted decision stumps based on application states specific to a particular application or a type of application, features, behaviors, conditions, or configurations to include subset or subsets of boosted decision stumps included in the full classifier model, and using the subset or subsets of boosted decision stumps to intelligently monitor, analyze and/or classify a mobile device behavior.

The use of boosted decision stumps allows the observer and/or analyzer modules to generate and apply lean data models without communicating with the cloud or a network to re-train the data, which significantly reduces the mobile device's dependence on the network server and the cloud. This eliminates the feedback communications between the mobile device and the network server, which further improves the performance and power consumption characteristics of the mobile device.

Boosted decision stumps are one level decision trees that have exactly one node (and thus one test question or test condition) and a weight value, and thus are well suited for use in a binary classification of data/behaviors. That is, applying a behavior vector to boosted decision stump results in a binary answer (e.g., Yes or No). For example, if the question/condition tested by a boosted decision stump is "is the frequency of Short Message Service (SMS) transmissions less than x per minute," applying a value of "3" to the boosted decision stump will result in either a "yes" answer (for "less than 3" SMS transmissions) or a "no" answer (for "3 or more" SMS transmissions).

Boosted decision stumps are efficient because they are very simple and primal (and thus do not require significant processing resources). Boosted decision stumps are also very parallelizable, and thus many stumps may be applied or tested in parallel/at the same time (e.g., by multiple cores or processors in the mobile device).

As described below, the network server (or another computing device) may generate a boosted decision stump-type full classifier model from another, more complex model of mobile device behaviors, such as a boosted decision tree model. Such complex models may correlate the full (or nearly full) set of interactions among device states, operations, and monitored nodes that characterize mobile device behavior in a sophisticated classification system. As mentioned above, the server or other computing device may generate a full, complex classifier model by applying machine learning techniques to generate models that describe a cloud corpus of behavior vectors of mobile devices collected from a large number of mobile devices. As an example, a boosted decision tree classifier model may trace hundreds of paths through decision nodes of testable conditions to arrive at a determination of whether a current mobile device behavior is malicious or benign. Such complex models may be generated in the server using a number of known learning and correlation modeling techniques. While such complex models can become quite effective in accurately recognizing malicious behaviors by learning from data from many hundreds of mobile devices, their application to a particular mobile device's configuration and behaviors may require significant processing, particularly if the model involves complex, multilevel decision trees. Since mobile devices are typically resource limited, using such models may impact device performance and battery life.

To render robust classifier models that are more conducive to use by mobile devices, a server (e.g., a cloud server or the network server) or another computing device (e.g., a mobile device or a computer that will couple to the mobile device) may transform complex classifier models into large boosted decision stump models. The more simple determinations involved in decision stumps and the ability to apply such classifier models in parallel processes may enable mobile devices to better benefit from the analyses performed by the network server. Also, as discussed below, a boosted decision stump full classifier model may be used by mobile devices to generate a lean classifier model to include (or exclude) features based on device-specific or device-state-specific information. This may be accomplished by configuring a mobile device processor to perform the aspect methods described below.

In further aspects, the mobile device may include various components configured to incorporate features specific to the mobile device or the mobile device's current state into a lean classifier model or a set of lean classifier models used to detect malicious behavior on the mobile device.

In an aspect, the mobile device may be configured to generate a lean classifier model to include a subset of classifier criteria included in the full classifier model that prioritizes classifier criteria corresponding to the features relevant to the mobile device configuration, functionality, and connected/included hardware. The mobile device may use this lean classifier model(s) to preferentially or exclusively monitor those features and functions present or relevant to the device. The mobile device may then periodically modify or regenerate the lean classifier model(s) to include or remove various features and corresponding classifier criteria based on the mobile device's current state and configuration.

As an example and in an aspect, a behavior analyzer module operating on the mobile device may receive a large boosted decision stumps classifier model with decision stumps associated with a full feature set of behavior models, and the behavior analyzer module may derive one or more lean classifier models from the large classifier models by selecting or prioritizing features from the large classifier model(s) that are relevant the mobile device's current configuration, functionality, operating state and/or connected/included hardware, and including in the lean classifier model a subset of boosted decision stumps that correspond to the selected features. In this aspect, the classifier criteria corresponding to features relevant to the mobile device may be those boosted decision stumps included in the large classifier model that test at least one of the selected features. In an aspect, the behavior analyzer module may then periodically modify or regenerate the boosted decision stumps lean classifier model(s) to include or remove various features based on the mobile device's current state and configuration so that the lean classifier model continues to include device-specific feature boosted decision stumps.

In an aspect, a device state monitoring engine operating on the mobile computing device may continually monitor the mobile device for changes in the mobile device's configuration and/or state. In a further aspect, the device state monitoring engine may look for configuration and/or state changes that may impact the performance or effectiveness of the behavior analyzer module (or a classifier module) to detect malicious behavior. For example, the device state monitoring engine may monitor the mobile device's behaviors until a "low battery state" is detected, at which point the behavior analyzer module may change the lean classifier model to analyze fewer features on the mobile device for malicious behavior in order to conserve energy.

In another aspect, the device state monitoring engine may notify a device state specific feature generator when the device state monitoring engine detects a state change, and the device state specific feature generator may signal the behavior analyzer module to add or remove certain features based on the mobile device's state change.

In another aspect, the mobile device may include a device specific feature generator configured to determine features related to the mobile device itself. For example, the device-specific feature generator may determine that the mobile device includes near-field communication, Wi-Fi, and Bluetooth® capabilities. In a further aspect, the device-specific feature generator may signal the behavior analyzer to include or remove features in the lean classifier models based on the features related to the mobile device itself. Thus, various components on the mobile device may modify a lean classifier model to reflect features specific to the mobile device's configuration and/or to the mobile device's current state, which may enable the various components to better detect malicious behavior or improve the overall performance of the mobile device by prioritizing monitored features based on the mobile device's current state.

As noted above, one example of a type of large classifier model that may be processed by a mobile device to generate a lean classifier model for use in monitoring behavior is a boosted decision stumps classifier model. In the detailed descriptions that follow references may be made to boosted decision stumps classifier models; however, such references are for example purposes, and are not intended to limit the scope of the claims unless a claim explicitly recites a boosted decision stumps classifier model.

In an aspect, the mobile device may be configured to generate an application-based classifier model by receiving a full classifier model that includes a plurality of test conditions from the network server, identifying the mobile device features that are used by a software application of the mobile device (or by a type of software application that may execute on the mobile device), identifying the test conditions in the full classifier model that evaluate one of identified mobile device features, determining the priority, importance or success rates of the identified test conditions, prioritizing or ordering the identified test conditions in accordance with their importance or success rates, and generating a classifier model that includes the identified test conditions so that they are ordered in accordance with their determined priorities, importance or success rates.

The mobile device may be configured to use the locally generated lean and/or application-based classifier models to perform real-time behavior monitoring and analysis operations. For example, the mobile device may use an application-based classifier model to classify the behavior of the mobile device executing corresponding application by collecting behavior information from the mobile device, using the collected behavior information to generate a feature vector, applying the generated feature vector to the application-based classifier model to evaluate each test condition included in the application-based classifier model. The mobile device may also compute a weighted average of each result of evaluating test conditions in the application-based classifier model, and use the weighted average to determine whether a mobile device behavior is malicious or benign.

The various aspects may be implemented within a variety of communication systems, such as the example communication system 100 illustrated in FIG. 1. A typical cell telephone network 104 includes a plurality of cell base stations 106 coupled to a network operations center 108, which operates to connect voice calls and data between mobile devices 102 (e.g., cell phones, laptops, tablets, etc.) and other network destinations, such as via telephone land lines (e.g., a POTS network, not shown) and the Internet 110. Communications between the mobile devices 102 and the telephone network 104 may be accomplished via two-way wireless communication links 112, such as 4G, 3G, CDMA, TDMA, LTE and/or other cell telephone communication technologies. The telephone network 104 may also include one or more servers 114 coupled to or within the network operations center 108 that provide a connection to the Internet 110.

The communication system 100 may further include network servers 116 connected to the telephone network 104 and to the Internet 110. The connection between the network servers 116 and the telephone network 104 may be through the Internet 110 or through a private network (as illustrated by the dashed arrows). A network server 116 may also be implemented as a server within the network infrastructure of a cloud service provider network 118. Communication between the network server 116 and the mobile devices 102 may be achieved through the telephone network 104, the internet 110, private network (not illustrated), or any combination thereof.

The network server 116 may be configured to receive information on various conditions, features, behaviors, and corrective actions from a central database or cloud service provider network 118, and use this information to generate data, algorithms, classifiers, or behavior models (herein collectively "classifier models") that include data and/or information structures (e.g., feature vectors, behavior vectors, component lists, etc.) that may be used by a processor of a computing device to evaluate a specific aspect of the computing device's behavior.

In an aspect, the network server 116 may be configured to generate a full classifier model. The full classifier model may be a robust data model that is generated as a function of a large training dataset, which may include thousands of features and billions of entries. In an aspect, the network server 116 may be configured to generate the full classifier model to include all or most of the features, data points, and/or factors that could contribute to the degradation of any of a number of different makes, models, and configurations of mobile devices 102. In various aspects, the network server may be configured to generate the full classifier model to describe or express a large corpus of behavior information as a finite state machine, decision nodes, decision trees, or in any information structure that can be modified, culled, augmented, or otherwise used to quickly and efficiently generate leaner classifier models.

In addition, the mobile device 102 may be configured to receive the full classifier model from the network server 116. The mobile device may be further configured to use the full classifier model to generate more focused classifier models that account for the specific features and functionalities of the software applications of the mobile device 102. For example, the mobile device 102 may generate application-specific and/or application-type-specific classifier models (i.e., data or behavior models) that preferentially or exclusively identify or evaluate the conditions or features of the mobile device that are relevant to a specific software application or to a specific type of software application (e.g., games, navigation, financial, etc.) that is installed on the mobile device 102 or stored in a memory of the device. The mobile device 102 may use these locally generated classifier models to perform real-time behavior monitoring and analysis operations.

Figure 2:
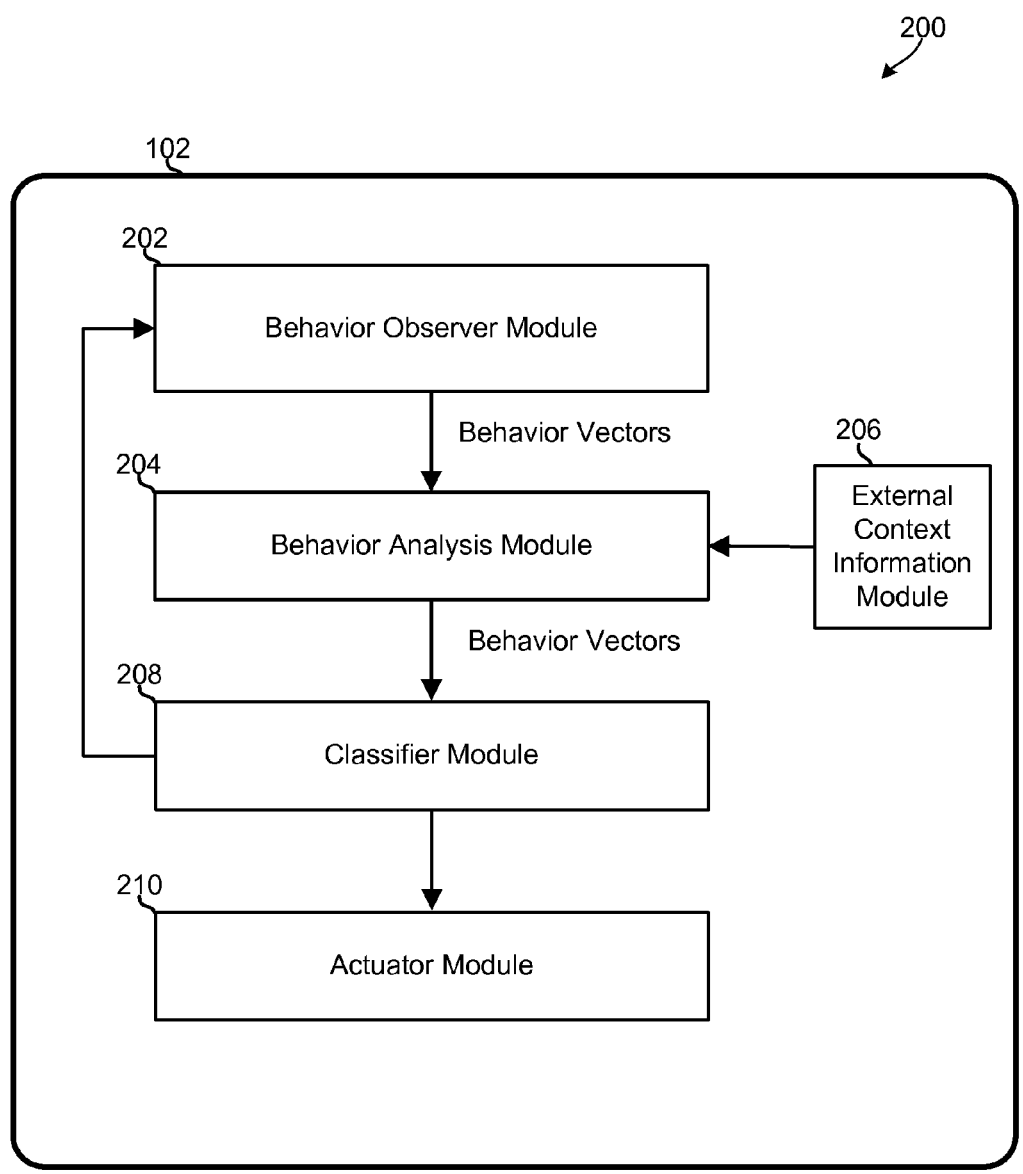
FIG. 2 is a block diagram illustrating example logical components and information flows in an aspect mobile device configured to determine whether a particular mobile device behavior is malicious, performance-degrading, suspicious, or benign.

FIG. 2 illustrates example logical components and information flows in an aspect mobile device 102 configured to perform real-time behavior monitoring and analysis operations 200 to determine whether a particular mobile device behavior, software application, or process is malicious/performance-degrading, suspicious, or benign. These operations 200 may be performed by one or more processing cores in the mobile device 102 continuously (or near continuously) without consuming an excessive amount of the mobile device's processing, memory, or energy resources.

In the example illustrated in FIG. 2, the mobile device 102 includes a behavior observer module 202, a behavior analyzer module 204, an external context information module 206, a classifier module 208, and an actuator module 210. In an aspect, the classifier module 208 may be implemented as part of the behavior analyzer module 204. In an aspect, the behavior analyzer module 204 may be configured to generate one or more classifier modules 208, each of which may include one or more classifier models (e.g., data/behavior models) that include data and/or information structures (e.g., decision nodes, etc.) that may be used by a mobile device processor to evaluate specific features of a software application or mobile device behavior.

Each of the modules 202-210 may be a thread, process, daemon, module, sub-system, or component that is implemented in software, hardware, or a combination thereof. In various aspects, the modules 202-210 may be implemented within parts of the operating system (e.g., within the kernel, in the kernel space, in the user space, etc.), within separate programs or applications, in specialized hardware buffers or processors, or any combination thereof. In an aspect, one or more of the modules 202-210 may be implemented as software instructions executing on one or more processors of the mobile device 102.

The behavior observer module 202 may be configured to instrument or coordinate various APIs, registers, counters or other components (herein collectively "instrumented components") at various levels of the mobile device system, and continuously (or near continuously) monitor mobile device behaviors over a period of time and in real-time by collecting behavior information from the instrumented components. For example, the behavior observer module 202 may monitor library API calls, system call APIs, driver API calls, and other instrumented components by reading information from log files (e.g., API logs, etc.) stored in a memory of the mobile device 102.

The behavior observer module 202 may also be configured to monitor/observe mobile device operations and events (e.g., system events, state changes, etc.) via the instrumented components, collect information pertaining to the observed operations/events, intelligently filter the collected information, generate one or more observations (e.g., behavior vectors, etc.) based on the filtered information, and store the generated observations in a memory (e.g., in a log file, etc.) and/or send (e.g., via memory writes, function calls, etc.) the generated observations or collected behavior information to the behavior analyzer module 204. In various aspects, the generated observations may be stored as a behavior vector and/or in an API log file or structure.

The behavior observer module 202 may monitor/observe mobile device operations and events by collecting information pertaining to library API calls in an application framework or run-time libraries, system call APIs, file-system, and networking sub-system operations, device (including sensor devices) state changes, and other similar events. The behavior observer module 202 may also monitor file system activity, which may include searching for filenames, categories of file accesses (personal info or normal data files), creating or deleting files (e.g., type exe, zip, etc.), file read/write/seek operations, changing file permissions, etc.

The behavior observer module 202 may also monitor data network activity, which may include types of connections, protocols, port numbers, server/client that the device is connected to, the number of connections, volume or frequency of communications, etc. The behavior observer module 202 may monitor phone network activity, which may include monitoring the type and number of calls or messages (e.g., SMS, etc.) sent out, received, or intercepted (e.g., the number of premium calls placed).

The behavior observer module 202 may also monitor the system resource usage, which may include monitoring the number of forks, memory access operations, number of files open, etc. The behavior observer module 202 may monitor the state of the mobile device, which may include monitoring various factors, such as whether the display is on or off, whether the device is locked or unlocked, the amount of battery remaining, the state of the camera, etc. The behavior observer module 202 may also monitor inter-process communications (IPC) by, for example, monitoring intents to crucial services (browser, contracts provider, etc.), the degree of inter-process communications, pop-up windows, etc.

The behavior observer module 202 may also monitor/observe driver statistics and/or the status of one or more hardware components, which may include cameras, sensors, electronic displays, WiFi communication components, data controllers, memory controllers, system controllers, access ports, timers, peripheral devices, wireless communication components, external memory chips, voltage regulators, oscillators, phase-locked loops, peripheral bridges, and other similar components used to support the processors and clients running on the mobile computing device.

The behavior observer module 202 may also monitor/observe one or more hardware counters that denote the state or status of the mobile computing device and/or mobile device sub-systems. A hardware counter may include a special-purpose register of the processors/cores that is configured to store a count or state of hardware-related activities or events occurring in the mobile computing device.

The behavior observer module 202 may also monitor/observe actions or operations of software applications, software downloads from an application download server (e.g., Apple® App Store server), mobile device information used by software applications, call information, text messaging information (e.g., SendSMS, BlockSMS, ReadSMS, etc.), media messaging information (e.g., ReceiveMMS), user account information, location information, camera information, accelerometer information, browser information, content of browser-based communications, content of voice-based communications, short range radio communications (e.g., Bluetooth®, WiFi, etc.), content of text-based communications, content of recorded audio files, phonebook or contact information, contacts lists, etc.

The behavior observer module 202 may monitor/observe transmissions or communications of the mobile device, including communications that include voicemail (VoiceMailComm), device identifiers (DeviceIDComm), user account information (UserAccountComm), calendar information (CalendarComm), location information (LocationComm), recorded audio information (RecordAudioComm), accelerometer information (AccelerometerComm), etc.

The behavior observer module 202 may monitor/observe usage of and updates/changes to compass information, mobile device settings, battery life, gyroscope information, pressure sensors, magnet sensors, screen activity, etc. The behavior observer module 202 may monitor/observe notifications communicated to and from a software application (AppNotifications), application updates, etc. The behavior observer module 202 may monitor/observe conditions or events pertaining to a first software application requesting the downloading and/or install of a second software application. The behavior observer module 202 may monitor/observe conditions or events pertaining to user verification, such as the entry of a password, etc.

The behavior observer module 202 may also monitor/observe conditions or events at multiple levels of the mobile device, including the application level, radio level, and sensor level. Application level observations may include observing the user via facial recognition software, observing social streams, observing notes entered by the user, observing events pertaining to the use of financial applications such as PassBook, Google® wallet, and Paypal, observing a software application's access and use of protected information, etc. Application level observations may also include observing events relating to the use of virtual private networks (VPNs) and events pertaining to synchronization, voice searches, voice control (e.g., lock/unlock a phone by saying one word), language translators, the offloading of data for computations, video streaming, camera usage without user activity, microphone usage without user activity, etc. The application level observation may also include monitoring a software application's use of biometric sensors (e.g., fingerprint reader, voice recognition subsystem, retina scanner, etc.) to authorize financial transactions, and conditions relating to the access and use of the biometric sensors.

Radio level observations may include determining the presence, existence or amount of any or more of: user interaction with the mobile device before establishing radio communication links or transmitting information, dual/multiple subscriber identity module (SIM) cards, Internet radio, mobile phone tethering, offloading data for computations, device state communications, the use as a game controller or home controller, vehicle communications, mobile device synchronization, etc. Radio level observations may also include monitoring the use of radios (WiFi, WiMax, Bluetooth, etc.) for positioning, peer-to-peer (p2p) communications, synchronization, vehicle to vehicle communications, and/or machine-to-machine (m2m). Radio level observations may further include monitoring network traffic usage, statistics, or profiles.

Sensor level observations may include monitoring a magnet sensor or other sensor to determine the usage and/or external environment of the mobile device. For example, the mobile device processor may be configured to determine whether the phone is in a holster (e.g., via a magnet sensor configured to sense a magnet within the holster) or in the user's pocket (e.g., via the amount of light detected by a camera or light sensor). Detecting that the mobile device is in a holster may be relevant to recognizing suspicious behaviors, for example, because activities and functions related to active usage by a user (e.g., taking photographs or videos, sending messages, conducting a voice call, recording sounds, etc.) occurring while the mobile device is holstered could be signs of nefarious processes executing on the device (e.g., to track or spy on the user).

Other examples of sensor level observations related to usage or external environments may include, detecting near-field communications (NFC), collecting information from a credit card scanner, barcode scanner, or mobile tag reader, detecting the presence of a universal serial bus (USB) power charging source, detecting that a keyboard or auxiliary device has been coupled to the mobile device, detecting that the mobile device has been coupled to a computing device (e.g., via USB, etc.), determining whether an LED, flash, flashlight, or light source has been modified or disabled (e.g., maliciously disabling an emergency signaling app, etc.), detecting that a speaker or microphone has been turned on or powered, detecting a charging or power event, detecting that the mobile device is being used as a game controller, etc. Sensor level observations may also include collecting information from medical or healthcare sensors or from scanning the user's body, collecting information from an external sensor plugged into the USB/audio jack, collecting information from a tactile or haptic sensor (e.g., via a vibrator interface, etc.), collecting information pertaining to the thermal state of the mobile device, collecting information from a fingerprint reader, voice recognition subsystem, retina scanner, etc.

The behavior observer module 202 may be configured to generate behavior vectors that include a concise definition of the observed behaviors. Each behavior vector may succinctly describe observed behavior of the mobile device, software application, or process in a value or vector datastructure (e.g., in the form of a string of numbers, etc.). A behavior vector may also function as an identifier that enables the mobile device system to quickly recognize, identify, and/or analyze mobile device behaviors. In an aspect, the behavior observer module 202 may generate a behavior vector that includes a series of numbers, each of which signifies a feature or a behavior of the mobile device.

For example, numbers included in the behavior vector may signify whether a camera of the mobile device is in use (e.g., as zero when the camera is off and one when the camera is activated), an amount of network traffic that has been transmitted from or generated by the mobile device (e.g., 20 KB/sec, etc.), a number of Internet messages that have been communicated (e.g., number of SMS messages, etc.), and so forth.

There may be a large variety of factors that may contribute to the degradation in performance and power utilization levels of the mobile device over time, including poorly designed software applications, malware, viruses, fragmented memory, and background processes. Due to the number, variety, and complexity of these factors, it is often not feasible to simultaneously evaluate all of the various components, behaviors, processes, operations, conditions, states, or features (or combinations thereof) that may degrade performance and/or power utilization levels of the complex yet resource-constrained systems of modern mobile devices. To reduce the number of factors monitored to a manageable level, in an aspect, the behavior observer module 202 may be configured to monitor/observe an initial or reduced set of behaviors or factors that are a small subset of all factors that could contribute to the mobile device's degradation.

In an aspect, the behavior observer module 202 may receive the initial set of behaviors and/or factors from a network server 116 and/or a component in a cloud service or network 118. In an aspect, the initial set of behaviors/factors may be specified in a full classifier model received from the network server 116. In another aspect, the initial set of behaviors/factors may be specified in a lean classifier model that is generated in the mobile device based on the full classifier model. In an aspect, the initial set of behaviors/factors may be specified in an application-based classifier model that is generated in the mobile device based on the full or lean classifier models. In various aspects, the application-based classifier model may be an application-specific classifier model or an application-type-specific classifier model.

The behavior observer module 202 may communicate (e.g., via a memory write operation, function call, etc.) collected behavior information to the behavior analyzer module 204. The behavior analyzer module 204 may receive and use the behavior information to generate behavior vectors, generate spatial and/or temporal correlations based on the behavior vectors, and use this information to determine whether a particular mobile device behavior, condition, sub-system, software application, or process is benign, suspicious, or not benign (i.e., malicious or performance-degrading).

The behavior analyzer module 204 and/or the classifier module 208 may be configured to perform real-time behavior analysis operations, which may include performing, executing, and/or applying data, algorithms, classifiers, or models (collectively referred to as "classifier models") to the collected behavior information to determine whether a mobile device behavior is benign or not benign (e.g., malicious or performance-degrading). Each classifier model may be a behavior model that includes data and/or information structures (e.g., feature vectors, behavior vectors, component lists, etc.) that may be used by a mobile device processor to evaluate a specific feature or aspect of a mobile device behavior. Each classifier model may also include decision criteria for monitoring (i.e., via the behavior observer module 202) a number of features, factors, data points, entries, APIs, states, conditions, behaviors, applications, processes, operations, components, etc. (collectively referred to as "features") in the mobile device 102. Classifier models may be preinstalled on the mobile device 102, downloaded or received from the network server 116, generated in the mobile device 102, or any combination thereof. The classifier models may also be generated by using crowd sourcing solutions, behavior modeling techniques, machine learning algorithms, etc.

Each classifier model may be categorized as a full classifier model or a lean classifier model. A full classifier model may be a robust data model that is generated as a function of a large training dataset, which may include thousands of features and billions of entries. A lean classifier model may be a more focused data model that is generated from a reduced dataset that includes or prioritizes tests on the features/entries that are most relevant for determining whether a particular mobile device behavior is benign or not benign (e.g., malicious or performance-degrading).

The behavior analyzer module 204 and/or classifier module 208 may receive the observations or behavior information from the behavior observer module 202, compare the received information (i.e., observations) with contextual information received from the external context information module 206, and identify subsystems, processes, and/or applications associated with the received observations that are contributing to (or are likely to contribute to) the device's degradation over time, or which may otherwise cause problems on the device.

In an aspect, the behavior analyzer module 204 and/or classifier module 208 may include intelligence for utilizing a limited set of information (i.e., coarse observations) to identify behaviors, processes, or programs that are contributing to—or are likely to contribute to—the device's degradation over time, or which may otherwise cause problems on the device. For example, the behavior analyzer module 204 may be configured to analyze information (e.g., in the form of observations) collected from various modules (e.g., the behavior observer module 202, external context information module 206, etc.), learn the normal operational behaviors of the mobile device, and generate one or more behavior vectors based the results of the comparisons. The behavior analyzer module 204 may send the generated behavior vectors to the classifier module 208 for further analysis.

In an aspect, the classifier module 208 may be configured to apply or compare behavior vectors to a classifier model to determine whether a particular mobile device behavior, software application, or process is performance-degrading/malicious, benign, or suspicious. When the classifier module 208 determines that a behavior, software application, or process is malicious or performance-degrading, the classifier module 208 may notify the actuator module 210, which may perform various actions or operations to correct mobile device behaviors determined to be malicious or performance-degrading and/or perform operations to heal, cure, isolate, or otherwise fix the identified problem.

When the classifier module 208 determines that a behavior, software application, or process is suspicious, the classifier module 208 may notify the behavior observer module 202, which may adjust the adjust the granularity of its observations (i.e., the level of detail at which mobile device behaviors are observed) and/or change the behaviors that are observed based on information received from the classifier module 208 (e.g., results of the real-time analysis operations), generate or collect new or additional behavior information, and send the new/additional information to the behavior analyzer module 204 and/or classifier module 208 for further analysis/classification. Such feedback communications between the behavior observer module 202 and the classifier module 208 enable the mobile device 102 to recursively increase the granularity of the observations (i.e., make finer or more detailed observations) or change the features/behaviors that are observed until a source of a suspicious or performance-degrading mobile device behavior is identified, until a processing or battery consumption threshold is reached, or until the mobile device processor determines that the source of the suspicious or performance-degrading mobile device behavior cannot be identified from further increases in observation granularity. Such feedback communication also enable the mobile device 102 to adjust or modify the data/behavior models locally in the mobile device without consuming an excessive amount of the mobile device's processing, memory, or energy resources.

In an aspect, the behavior observer module 202 and the behavior analyzer module 204 may provide, either individually or collectively, real-time behavior analysis of the computing system's behaviors to identify suspicious behavior from limited and coarse observations, to dynamically determine behaviors to observe in greater detail, and to dynamically determine the level of detail required for the observations. In this manner, the behavior observer module 202 enables the mobile device 102 to efficiently identify and prevent problems from occurring on mobile devices without requiring a large amount of processor, memory, or battery resources on the device.

In various aspects, the behavior observer module 202 and/or the behavior analyzer module 204 may be configured to analyze mobile device behaviors by identifying a critical data resource that requires close monitoring, identifying an intermediate resource associated with the critical data resource, monitoring API calls made by a software application when accessing the critical data resource and the intermediate resource, identifying mobile device resources that are consumed or produced by the API calls, identifying a pattern of API calls as being indicative of malicious activity by the software application, generating a light-weight behavior signature based on the identified pattern of API calls and the identified mobile device resources, using the light-weight behavior signature to perform behavior analysis operations, and determining whether the software application is malicious or benign based on the behavior analysis operations.

In various aspects, the behavior observer module 202 and/or the behavior analyzer module 204 may be configured to analyze mobile device behaviors by identifying APIs that are used most frequently by software applications executing on the mobile device, storing information regarding usage of identified hot APIs in an API log in a memory of the mobile device, and performing behavior analysis operations based on the information stored in the API log to identify mobile device behaviors that are inconsistent with normal operation patterns. In an aspect, the API log may be generated so that it is organized such that that the values of generic fields that remain the same across invocations of an API are stored in a separate table as the values of specific fields that are specific to each invocation of the API. The API log may also be generated so that the values of the specific fields are stored in a table along with hash keys to the separate table that stores the values of the generic fields.

In various aspects, the behavior observer module 202 and/or the behavior analyzer module 204 may be configured to analyze mobile device behaviors by receiving a full classifier model that includes a finite state machine that is suitable for conversion or expression as a plurality of boosted decision stumps, generating a lean classifier model in the mobile device based on the full classifier, and using the lean classifier model in the mobile device to classify a behavior of the mobile device as being either benign or not benign (i.e., malicious, performance degrading, etc.). In an aspect, generating the lean classifier model based on the full classifier model may include determining a number of unique test conditions that should be evaluated to classify a mobile device behavior without consuming an excessive amount of processing, memory, or energy resources of the mobile device, generating a list of test conditions by sequentially traversing the list of boosted decision stumps and inserting the test condition associated with each sequentially traversed boosted decision stump into the list of test conditions until the list of test conditions may include the determined number of unique test conditions, and generating the lean classifier model to include or prioritize those boosted decision stumps that test one of a plurality of test conditions included in the generated list of test conditions.

In various aspects, the behavior observer module 202 and/or the behavior analyzer module 204 may be configured to use device-specific information of the mobile device to identify mobile device-specific, application-specific, or application-type specific test conditions in a plurality of test conditions that are relevant to classifying a behavior of the mobile device, generate a lean classifier model that includes or prioritizes the identified mobile device-specific, application-specific, or application-type specific test conditions, and use the generated lean classifier model in the mobile device to classify the behavior of the mobile device. In an aspect, the lean classifier model may be generated to include or prioritize decision nodes that evaluate a mobile device feature that is relevant to a current operating state or configuration of the mobile device. In a further aspect, generating the lean classifier model may include determining a number of unique test conditions that should be evaluated to classify the behavior without consuming an excessive amount of mobile device's resources (e.g., processing, memory, or energy resources), generating a list of test conditions by sequentially traversing the plurality of test conditions in the full classifier model, inserting those test conditions that are relevant to classifying the behavior of the mobile device into the list of test conditions until the list of test conditions includes the determined number of unique test conditions, and generating the lean classifier model to include decision nodes included in the full classifier model that test one of the conditions included in the generated list of test conditions.

In various aspects, the behavior observer module 202 and/or the behavior analyzer module 204 may be configured to recognize mobile device behaviors that are inconsistent with normal operation patterns of the mobile device by monitoring an activity of a software application or process, determining an operating system execution state of the software application/process, and determining whether the activity is benign based on the activity and/or the operating system execution state of the software application or process during which the activity was monitored. In an further aspect, the behavior observer module 202 and/or the behavior analyzer module 204 may determine whether the operating system execution state of the software application or process is relevant to the activity, generate a shadow feature value that identifies the operating system execution state of the software application or process during which the activity was monitored, generate a behavior vector that associates the activity with the shadow feature value identifying the operating system execution state, and use the behavior vector to determine whether the activity is benign, suspicious, or not benign (i.e., malicious or performance-degrading).

As discussed above, a mobile device processor may receive or generate a classifier model that includes a plurality of test conditions suitable for evaluating various features, identify the mobile device features used by a specific software application or software application-type, identify the test conditions in the received/generated classifier model that evaluate the identified mobile device features, and generate an application-specific and/or application-type specific classifier models that include or prioritize the identified test conditions. The features used by the specific software application or a specific software application-type may be determined by monitoring or evaluating mobile device operations, mobile device events, data network activity, system resource usage, mobile device state, inter-process communications, driver statistics, hardware component status, hardware counters, actions or operations of software applications, software downloads, changes to device or component settings, conditions and events at an application level, conditions and events at the radio level, conditions and events at the sensor level, location hardware, personal area network hardware, microphone hardware, speaker hardware, camera hardware, screen hardware, universal serial bus hardware, synchronization hardware, location hardware drivers, personal area network hardware drivers, near field communication hardware drivers, microphone hardware drivers, speaker hardware drivers, camera hardware drivers, gyroscope hardware drivers, browser supporting hardware drivers, battery hardware drivers, universal serial bus hardware drivers, storage hardware drivers, user interaction hardware drivers, synchronization hardware drivers, radio interface hardware drivers, and location hardware, near field communication (NFC) hardware, screen hardware, browser supporting hardware, storage hardware, accelerometer hardware, synchronization hardware, dual SIM hardware, radio interface hardware, and features unrelated related to any specific hardware.

For example, in various aspects, the mobile device processor may identify mobile device features used by a specific software application (or specific software application type) by collecting information from one or more instrumented components, such as an inertia sensor component, a battery hardware component, a browser supporting hardware component, a camera hardware component, a subscriber identity module (SIM) hardware component, a location hardware component, a microphone hardware component, a radio interface hardware component, a speaker hardware component, a screen hardware component, a synchronization hardware component, a storage component, a universal serial bus hardware component, a user interaction hardware component, an inertia sensor driver component, a battery hardware driver component, a browser supporting hardware driver component, a camera hardware driver component, a SIM hardware driver component, a location hardware driver component, a microphone hardware driver component, a radio interface hardware driver component, a speaker hardware driver component, a screen hardware driver component, a synchronization hardware driver component, a storage driver component, a universal serial bus hardware driver component, a hardware component connected through a universal serial bus, and a user interaction hardware driver component.

In various aspects, the mobile device processor may identify mobile device features used by a specific software application (or specific software application type) by monitoring or analyzing one or more of library application programming interface (API) calls in an application framework or run-time library, system call APIs, file-system and networking sub-system operations, file system activity, searches for filenames, categories of file accesses, changing of file permissions, operations relating to the creation or deletion of files, and file read/write/seek operations.

In various aspects, the mobile device processor may identify mobile device features used by a specific software application (or specific software application type) by monitoring or analyzing one or more of connection types, protocols, port numbers, server/client that the device is connected to, the number of connections, volume or frequency of communications, phone network activity, type and number of calls/messages sent, type and number of calls/messages received, type and number of calls/messages intercepted, call information, text messaging information, media messaging, user account information, transmissions, voicemail, and device identifiers.

In various aspects, the mobile device processor may identify mobile device features used by a specific software application (or specific software application type) by monitoring or analyzing one or more of the number of forks, memory access operations, and the number of files opened by the software application. In various aspects, the mobile device processor may identify mobile device features used by a specific software application (or specific software application type) by monitoring or analyzing state changes caused by the software application, including a display on/off state, locked/unlocked state, battery charge state, camera state, and microphone state.

In various aspects, the mobile device processor may identify mobile device features used by a specific software application (or specific software application type) by monitoring or analyzing crucial services, a degree of inter-process communications, and pop-up windows generated by the software application. In various aspects, the mobile device processor may identify mobile device features used by a specific software application (or specific software application type) by monitoring or analyzing statistics from drivers for one or more of cameras, sensors, electronic displays, WiFi communication components, data controllers, memory controllers, system controllers, access ports, peripheral devices, wireless communication components, and external memory chips.

In various aspects, the mobile device processor may identify mobile device features used by a specific software application (or specific software application type) by monitoring or analyzing the access or use of cameras, sensors, electronic displays, WiFi communication components, data controllers, memory controllers, system controllers, access ports, timers, peripheral devices, wireless communication components, external memory chips, voltage regulators, oscillators, phase-locked loops, peripheral bridges, and other similar components used to support the processors and clients running on the mobile computing device.

In various aspects, the mobile device processor may identify mobile device features used by a specific software application (or specific software application type) by monitoring or analyzing the access or use of hardware counters that denote the state or status of the mobile computing device and/or mobile device sub-systems and/or special-purpose registers of processors/cores that are configured to store a count or state of hardware-related activities or events.

In various aspects, the mobile device processor may identify mobile device features used by a specific software application (or specific software application type) by monitoring or analyzing the types of information used by the software application, including location information, camera information, accelerometer information, browser information, content of browser-based communications, content of voice-based communications, short range radio communications, content of text-based communications, content of recorded audio files, phonebook or contact information, contacts lists, calendar information, location information, recorded audio information, accelerometer information, notifications communicated to and from a software application, user verifications, and a user password.

In various aspects, the mobile device processor may identify mobile device features used by a specific software application (or specific software application type) by monitoring or analyzing one or more of software downloads from an application download server, and a first software application requesting the downloading and/or install of a second software application.

Figure 3:
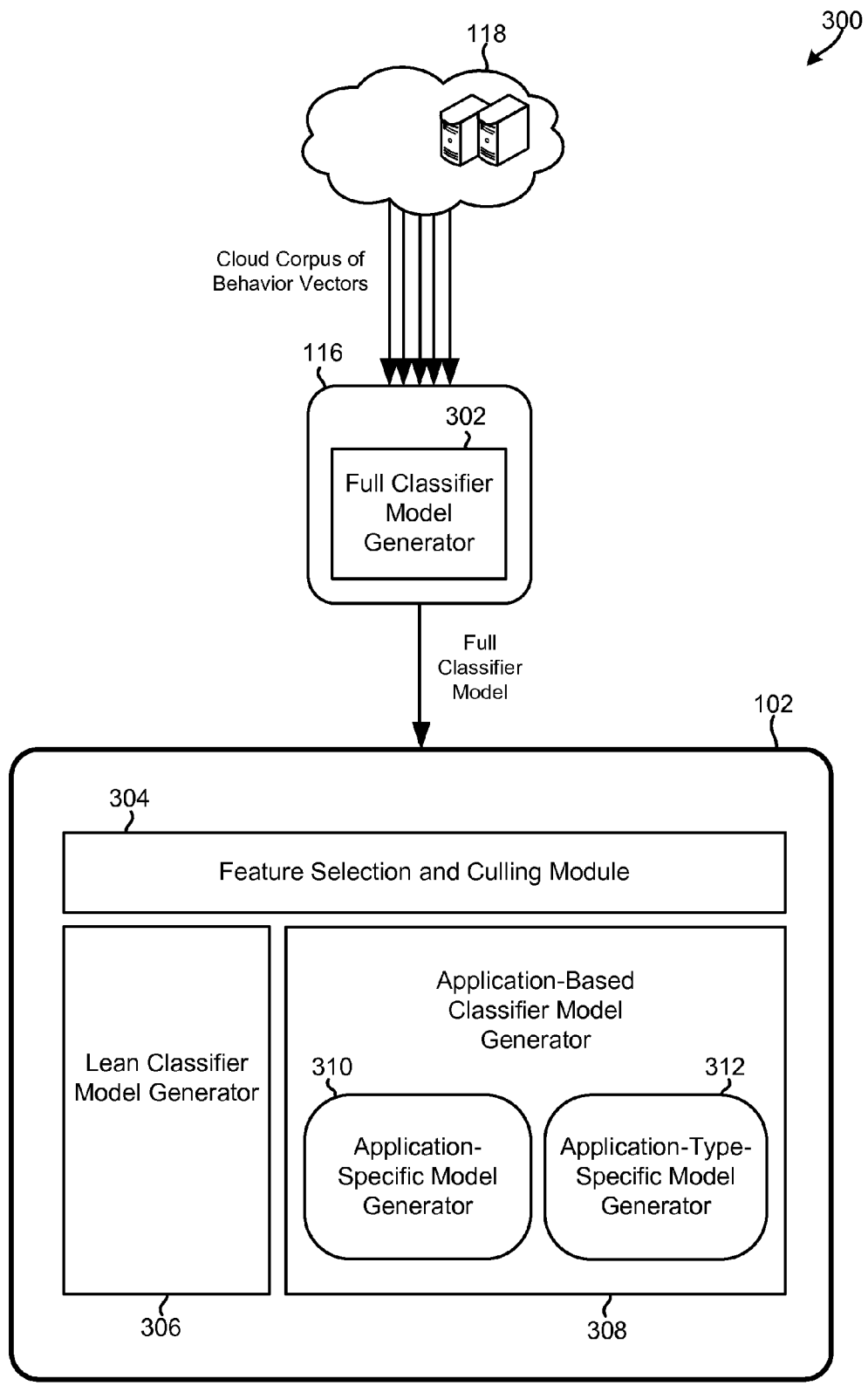
FIG. 3 is a block diagram illustrating example components and information flows in an aspect system that includes a network server configured to work in conjunction with a mobile device to determine whether a particular mobile device behavior is malicious, performance-degrading, suspicious, or benign.

FIG. 3 illustrates example components and information flows in a system 300 that includes a network server 116 configured to work in conjunction with the mobile device 102 to intelligently and efficiently identify performance-degrading mobile device behaviors on the mobile device 102 without consuming an excessive amount of processing, memory, or energy resources of the mobile device 102. In the example illustrated in FIG. 3, the mobile device 102 includes a feature selection and culling module 304, a lean classifier model generator module 306, and a application-based classifier model generator module 308, which may include an application-specific classifier model generator module 310 and an application-type-specific classifier model generator module 312. The network server 116 includes a full classifier model generator module 302.

Any or all of the modules 304-312 may be a real-time online classifier module and/or included in the behavior analyzer module 204 or classifier module 208 illustrated in FIG. 2. In an aspect, the application-based classifier model generator module 308 may be included in the lean classifier model generator module 306. In various aspects, the feature selection and culling module 304 may be included in the application-based classifier model generator module 308 or in the lean classifier model generator module 306.

The network server 116 may be configured to receive information on various conditions, features, behaviors, and corrective actions from the cloud service/network 118, and use this information to generate a full classifier model that describes a large corpus of behavior information in a format or structure that can be quickly converted into one or more lean classifier models by the mobile device 102. For example, the full classifier model generator module 302 in the network server 116 may use a cloud corpus of behavior vectors received from the cloud service/network 118 to generate a full classifier model, which may include a finite state machine description or representation of the large corpus of behavior information. The finite state machine may be an information structure that may be expressed as one or more decision nodes, such as a family of boosted decision stumps that collectively identify, describe, test, or evaluate all or many of the features and data points that are relevant to classifying mobile device behavior.

The network server 116 may send the full classifier model to the mobile device 102, which may receive and use the full classifier model to generate a reduced feature classifier model or a family of classifier models of varying levels of complexity or leanness. In various aspects, the reduced feature classifier models may be generated in the feature selection and culling module 304, lean classifier model generator module 306, the application-based classifier generator module 308, or any combination thereof. That is, the feature selection and culling module 304, lean classifier model generator module 306, and/or application-based classifier generator 308 modules of the mobile device 102 may, collectively or individually, use the information included in the full classifier model received from the network server to generate one or more reduced feature classifier models that include a subset of the features and data points included in full classifier model.

For example, the lean classifier model generator module 306 and feature selection and culling module 304 may collectively cull the robust family of boosted decision stumps included in the finite state machine of the full classifier model received from the network server 116 to generate a reduced feature classifier model that includes a reduced number of boosted decision stumps and/or evaluates a limited number of test conditions. The culling of the robust family of boosted decision stumps may be accomplished by selecting a boosted decision stump, identifying all other boosted decision stumps that test or depend upon the same mobile device feature as the selected decision stump, and adding the selected stump and all the identified other boosted decision stumps that test or depend upon the same mobile device feature to an information structure. This process may then be repeated for a limited number of stumps or device features, so that the information structure includes all boosted decision stumps in the full classifier model that test or depend upon a small or limited number of different features or conditions. The mobile device may then use this information structure as a lean classifier model to test a limited number of different features or conditions of the mobile device, and to quickly classify a mobile device behavior without consuming an excessive amount of its processing, memory, or energy resources.

The lean classifier model generator module 306 may be further configured to generate classifier models that are specific to the mobile device and to a particular software application or process that may execute on the mobile device. In this manner, one or more lean classifier models may be generated that preferentially or exclusively test features or elements that pertain to the mobile device and that are of particular relevance to the software application. These device- and application-specific/application type-specific lean classifier models may be generated by the lean classifier model generator module 306 in one pass by selecting test conditions that are relevant to the application and pertain to the mobile device. Alternatively, the lean classifier model generator module 306 may generate a device-specific lean classifier model including test conditions pertinent to the mobile device, and from this lean classifier model, generate a further refined model that includes or prioritize those test conditions that are relevant to the application. As a further alternative, the lean classifier model generator module 306 may generate a lean classifier model that is relevant to the application, and then remove test conditions that are not relevant to mobile device. For ease of description, the processes of generating a device-specific lean classifier model are described first, followed by processes of generating an application-specific or application-type specific lean classifier model.

The lean classifier model generator module 306 may be configured to generate device-specific classifier models by using device-specific information of the mobile device 102 to identify mobile device-specific features (or test conditions) that are relevant or pertain to classifying a behavior of that specific mobile device 102. The lean classifier model generator module 306 may use this information to generate the lean classifier models that preferentially or exclusively include, test, or depend upon the identified mobile device-specific features or test conditions. The mobile device 102 may then use these locally generated lean classifier models to classify the behavior of the mobile device without consuming an excessive amount of its processing, memory, or energy resources. That is, by generating the lean classifier models locally in the mobile device 102 to account for device-specific or device-state-specific features, the various aspects allow the mobile device 102 to focus its monitoring operations on the features or factors that are most important for identifying the source or cause of an undesirable behavior in that specific mobile device 102.

The lean classifier model generator module 306 may also be configured to determine whether an operating system execution state of the software application/process is relevant to determining whether any of the monitored mobile device behaviors are malicious or suspicious, and generate a lean classifier model that includes, identifies, or evaluates features or behaviors that take the operating system execution states into account. The mobile device 102 may then use these locally generated lean classifier models to preferentially or exclusively monitor the operating system execution states of the software applications for which such determinations are relevant. This allows the mobile device 102 to focus its operations on the most important features and functions of an application in order to better predict whether a behavior is benign. That is, by monitoring the operating system execution states of select software applications (or processes, threads, etc.), the various aspects allow the mobile device 102 to better predict whether a behavior is benign or malicious. Further, by intelligently determining whether the operating system execution state of a software application is relevant to the determination of whether a behavior is benign or malicious—and selecting for monitoring the software applications (or processes, threads, etc.) for which such determinations are relevant—the various aspects allow the mobile device 102 to better focus its operations and identify performance-degrading behaviors/factors without consuming an excessive amount of processing, memory, or energy resources of the mobile device.

In an aspect, the feature selection and culling module 304 may be configured to allow for feature selection and generation of classifier models "on the fly" and without requiring that the mobile device 102 to access the cloud data for retraining. This allows the application-based classifier model generator module 308 to generate/create classifier models in the mobile device 102 that allow the mobile device 102 to focus its operations on evaluating the features that relate to specific software applications or to specific types, classes, or categories of software applications.

That is, the application-based classifier model generator module 308 allows the mobile device 102 to generate and use highly focused and lean classifier models that preferentially or exclusively test or evaluate the features of the mobile device that are associated with an operation of a specific software application or with the operations that are typically performed by a certain type, class, or category of software applications. To accomplish this, the application-based classifier model generator module 308 may intelligently identify software applications that are at high-risk for abuse and/or are have a special need for security, and for each of these identified applications, determine the activities that the application can or will perform during its execution. The application-specific classifier model generator module 308 may then associate these activities with data centric features of the mobile device to generate classifier models that are well suited for use by the mobile device in determining whether an individual software application is contributing to, or is likely to contribute to, a performance degrading behavior of the mobile device 102.

The application-specific classifier model generator module 308 may be configured to generate application-specific and/or application-type-specific classifier models every time a new application is installed or updated in the mobile device. This may be accomplished via the application specific model generator module 310 and/or application-type-specific model generator module 312.

The application-type-specific classifier model generator module 312 may be configured to generate a classifier model for a specific software application based on a category, type, or classification of that software application (e.g. game, navigation, financial, etc.). The application-type-specific classifier model generator module 312 may determine the category, type, or classification of the software application by reading an application store label associated with the software application, by performing static analysis operations, and/or by comparing the software application to other similar software applications.

For example, the application-type-specific classifier model generator module 312 may evaluate the permissions (e.g., operating system, file, access, etc.) and/or API usage patterns of a first software application, compare this information to the permissions or API usage pattern of a second software application to determine whether the first software application includes the same set of permissions or utilizes the same set of APIs as the second software application, and use labeling information of the second software application to determine a software application type (e.g., financial software, banking application, etc.) for the first software application when the first software application includes the same set of permissions or utilizes the same set of APIs as the second software application. The application-type-specific classifier model generator module 312 may then generate, update, or select a classifier model that is suitable for evaluating the first software application based on the determined software application type. In an aspect, this may be achieved by culling the decision nodes included in the full classifier model received from the network server 116 based on the determined software application type.

The application-specific classifier model generator module 310 may be configured to generate a classifier model for a specific software application based on labeling information, static analysis, install time analysis, or by determining the operating system, file, and/or access permissions of the software application. For example, the mobile device may perform static analysis of the software application each time the software application is updated, store the results of this analysis in a memory of the mobile device, use this information to determine the mobile device conditions or factors that are most important for determining whether that application is contributing to a suspicious mobile device behavior, and cull the decision nodes included in the full classifier model to include nodes that test the most important conditions or factors.

Figure 4:
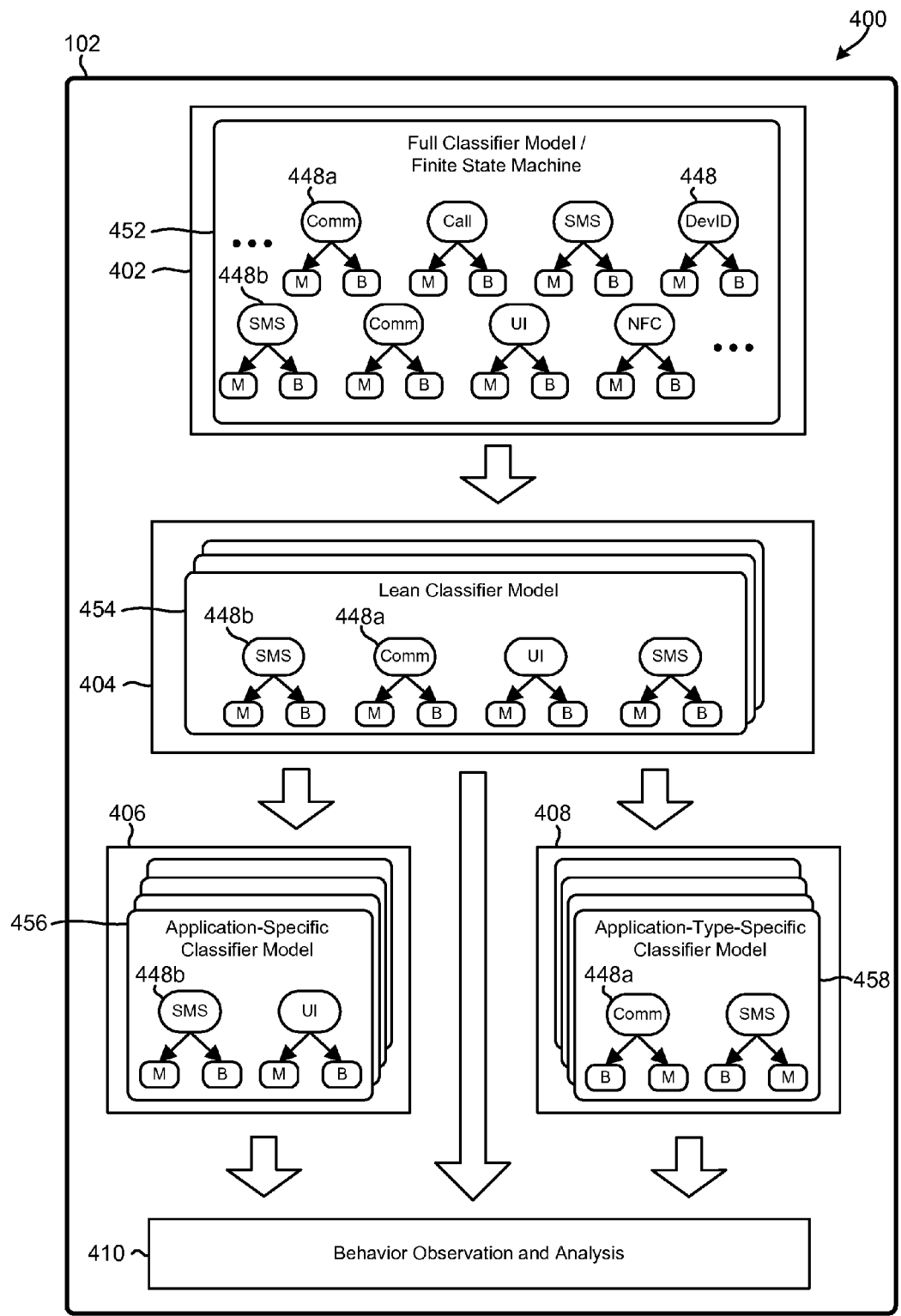
FIG. 4 is a block diagram illustrating example components and information flows in an aspect system that includes a mobile device configured to generate an application-based classifier models without re-training the data, behavior vectors, or classifier models.

FIG. 4 illustrates an aspect method 400 of generating application-specific and/or application-type-specific classifier models in a mobile device 102. Method 400 may be performed by a processing core of a mobile device 102.

In block 402, the processing core may use information included in a full classifier model 452 to generate a large number of decision nodes 448 that collectively identify, describe, test, or evaluate all or many of the features and data points that are relevant to determining whether a mobile device behavior is benign or contributing to the degradation in performance or power consumption characteristics of the mobile device 102 over time. For example, in block 402, the processing core may generate one-hundred (100) decision nodes 448 that test forty (40) unique conditions.

In an aspect, the decision nodes 448 may be decision stumps (e.g., boosted decision stumps, etc.). Each decision stump may be a one level decision tree that has exactly one node that tests one condition or mobile device feature. Because there is only one node in a decision stump, applying a feature vector to a decision stump results in a binary answer (e.g., yes or no, malicious or benign, etc.). For example, if the condition tested by a decision stump 448b is "is the frequency of SMS transmissions less than x per min," applying a value of "3" to the decision stump 448b will result in either a "yes" answer (for "less than 3" SMS transmissions) or a "no" answer (for "3 or more" SMS transmissions). This binary "yes" or "no" answer may then be used to classify the result as indicating that the behavior is either malicious (M) or benign (B). Since these stumps are very simple evaluations (basically binary), the processing to perform each stump is very simple and can be accomplished quickly and/or in parallel with less processing overhead.

In an aspect, each decision node 448 may be associated a weight value that is indicative of how much knowledge is gained from answering the test question and/or the likelihood that answering the test condition will enable the processing core to determine whether a mobile device behavior is benign. The weight associated with a decision node 448 may be computed based on information collected from previous observations or analysis of mobile device behaviors, software applications, or processes in the mobile device. In an aspect, the weight associated with each decision node 448 may also be computed based on how many units of the corpus of data (e.g., cloud corpus of data or behavior vectors) are used to build the node. In an aspect, the weight values may be generated based on the accuracy or performance information collected from the execution/application of previous data/behavior models or classifiers.

Returning to FIG. 4, in block 404, the processing core may generate a lean classifier model 454 that includes a focused subset of the decision nodes 448 included in the full classifier model 452. To accomplish this, the processing core may perform feature selection operations, which may include generating an ordered or prioritized list of the decision nodes 448 included in the full classifier model 452, determining a number of unique test conditions that should be evaluated to classify a mobile device behavior without consuming an excessive amount of processing, memory, or energy resources of the mobile device 102, generating a list of test conditions by sequentially traversing the ordered/prioritized list of decision nodes 448 and inserting a test condition associated with each sequentially traversed decision node 448 into the list of test conditions until the list of test conditions includes the determined number of unique test conditions, and generating an information structure that preferentially or exclusively includes the decision nodes 448 that test one of the test conditions included in the generated list of test conditions. In an aspect, the processing core may generate a family classifier models so that each model 454 in the family of classifier models evaluates a different number of unique test conditions and/or includes a different number of decision nodes.

In block 406, the processing core may trim, cull, or prune the decision nodes (i.e., boosted decision stumps) included in one of the lean classifier models 454 to generate an application-specific classifier model 456 that preferentially or exclusively includes the decision nodes in the lean classifier model 454 that test or evaluate conditions or features that are relevant to a specific software application (i.e., Google® wallet), such as by dropping decision nodes that address API's or functions that are not called or invoked by the application, as well as dropping decision nodes regarding device resources that are not accessed or modified by the application. In an aspect, the processing core may generate the application-specific classifier model 456 by performing feature selection and culling operations. In various aspects, the processing core may identify decision nodes 448 for inclusion in a application-specific classifier model 456 based on labeling information associated with a software application, the results of performing static analysis operations on the application, the results of performing install time analysis of the application, by evaluating the operating system, file, and/or access permissions of the software application, by evaluating the API usage of the application, etc.

In an aspect, in block 406, the processing core may generate a plurality of application-specific classifier models 456, each of which evaluate a different software application. In an aspect, the processing core may generate an application-specific classifier model 456 for every software application in the system and/or so that every application running on the mobile device has its own active classifier. In an aspect, in block 406, the processing core may generate a family of application-specific classifier models 456. Each application-specific classifier model 456 in the family of application-specific classifier models 456 may evaluate a different combination or number of the features that are relevant to a single software application.

In block 408, the processing core may trim, cull, or prune the decision nodes (i.e., boosted decision stumps) included in one of the lean classifier models 454 to generate application-type-specific classifier models 458. The generated application-type specific classifier models 458 may preferentially or exclusively include the decision nodes that are included in the full or lean classifier models 452, 454 that test or evaluate conditions or features that are relevant to a specific type, category, or class of software applications (e.g. game, navigation, financial, etc.). In an aspect, the processing core may identify the decision nodes for inclusion in the application-type specific classifier model 458 by performing feature selection and culling operations. In an aspect, the processing core may determine the category, type, or classification of each software application and/or identify the decision nodes 448 that are to be included in a application-type-specific classifier model 456 by reading an application store label associated with the software application, by performing static analysis operations, and/or by comparing the software application to other similar software applications.

In block 410, the processing core may use one or any combination of the locally generated classifier models 454, 456, 458 to perform real-time behavior monitoring and analysis operations, and predict whether a complex mobile device behavior is benign or contributing to the degradation of the performance or power consumption characteristics of the mobile device. In an aspect, the mobile device may be configured use or apply multiple classifier models 454, 456, 458 in parallel. In an aspect, the processing core may give preference or priority to the results generated from applying or using application-based classifier models 456, 458 over the results generated from applying/using the lean classifier model 454 when evaluating a specific software application.

The processing core may use the results of applying the classifier models to predict whether a complex mobile device behavior is benign or contributing to the degradation of the performance or power consumption characteristics of the mobile device over time.

By dynamically generating the application-based classifier models 456, 458 locally in the mobile device to account for application-specific or application-type-specific features and/or functionality, the various aspects allow the mobile device 102 to focus its monitoring operations on a small number of features that are most important for determining whether the operations of a specific software application are contributing to an undesirable or performance depredating behavior of the mobile device. This improves the performance and power consumption characteristics of the mobile device 102, and allows the mobile device to perform the real-time behavior monitoring and analysis operations continuously or near continuously without consuming an excessive amount of its processing, memory, or energy resources.

Figure 5A:
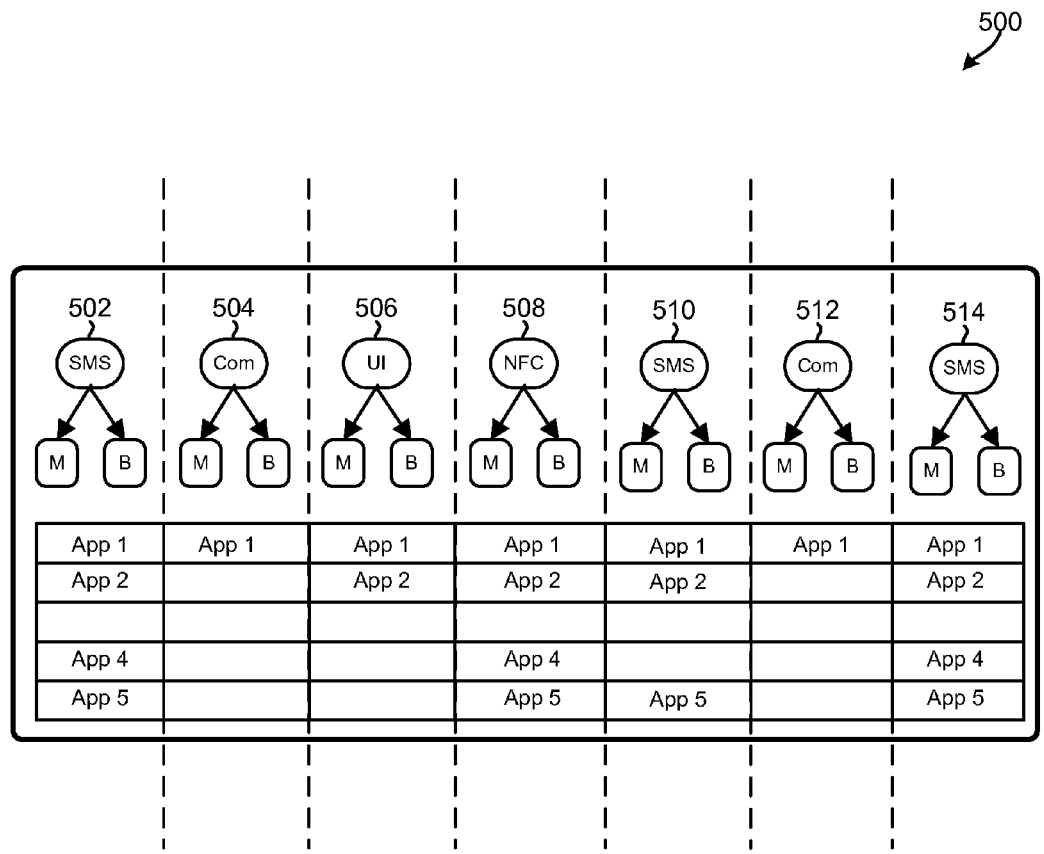
FIG. 5A is an illustration of an example classifier model mapped to a plurality of software applications.

FIG. 5A illustrates an example classifier model 500 that may be used by an aspect mobile device 102 to apply a behavior vector to multiple application-based classifier models in parallel. The classifier model 500 may be a full classifier model or a locally generated lean classifier model. The classifier model 500 may include a plurality of decision nodes 502-514 that are associated with one or more software applications App1-App5. For example, in FIG. 5A decision node 502 is associated with software applications App1, App2, App4, and App5, decision node 504 is associated with App1, decision node 506 is associated with App1 and App2, decision node 508 is associated with software applications App1, App2, App4, and App5, decision node 510 is associated with software applications App1, App2, and App5, decision node 512 is associated with software applications App1, and decision node 514 is associated with software applications App1, App2, App4, and App5.

In an aspect, a processing core in the mobile device may be configured to use the mappings between the decision nodes 502-514 and the software applications App1-App5 to partition the classifier model 500 into a plurality of application-based classifier models. For example, the processor may use the mappings to determine that an application-based classifier for App1 should include decision nodes 502-514, whereas an application-based classifier for App1 should include decision nodes 502, 506, 508, 510, and 514. That is, rather than generating and executing a different classifier model for each software application, the processing core may apply a behavior vector to all the decision nodes 502-514 included in the classifier model 500 to execute the same set of decision nodes 502-514 for all the classifiers. For each application App1-App5, the mobile device may apply a mask (e.g., a zero-one mask) to the classifier model 500 so that the decision nodes 502-514 that are relent to the application App1-App5 are used or prioritized to evaluate device behaviors when that application is executing.

In an aspect, the mobile device may calculate different weight values or different weighted averages for the decision nodes 502-514 based on their relevance to their corresponding application App1-App5. Computing such a confidence for the malware/benign value may include evaluating a number of decision nodes 502-514 and taking a weighted average of their weight values. In an aspect, the mobile device may compute the confidence value over the same or different lean classifiers. In an aspect, the mobile device may compute different weighted averages for each combination of decision nodes 502-514 that make up a classifier.

Figure 5B:
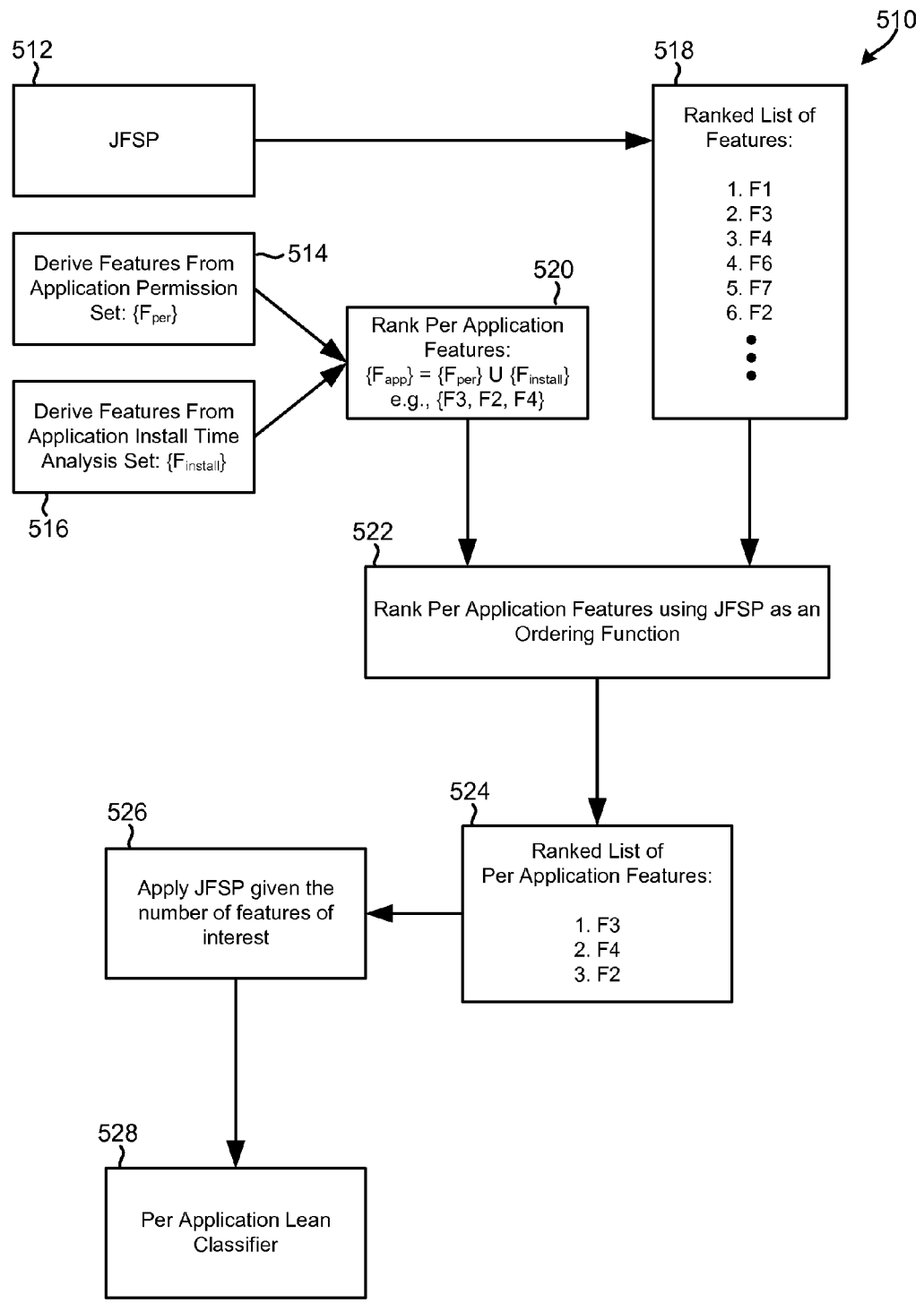
FIG. 5B is a process flow diagram illustrating another aspect mobile device method of generating application-based classifier models locally in the mobile device.

FIG. 5B illustrates an aspect method 510 of generating classifier models that account for application-specific and application-type-specific features of a mobile device. Method 510 may be performed by a processing core in a mobile device.

In block 512, the processing core may perform joint feature selection and culling (JFSP) operations to generate a lean classifier model that includes a reduced number of decision nodes and features/test conditions. In block 518, the processing core may prioritize or rank the features/test conditions in accordance with their relevance to classifying a behavior of the mobile device.

In block 514, the processing core may derive or determine features/test conditions for a software application by evaluating that application's permission set {Fper}. In block 516, the processing core may determine the set of features or test conditions {Finstall} for a software application by evaluating the results of performing static or install time analysis on that application. In block 520, the processing core may prioritize or rank the features/test conditions for each application in accordance with their relevance to classifying a behavior of the mobile device. In an aspect, this may be accomplished by via the formula:

$$\{Fapp\}=\{Fper\}U\{Finstall\}$$

In block 522, the processing core may prioritize or rank the per application features {Fapp} by using JFSP as an ordering function. For example, the processing core may perform JFSP operations on the lean classifier generated in block 518. In block 524, the processing core may generate the ranked list of per application features {Fapp}. In block 526, the processing core may apply JFSP to select the features of interest. In block 528, the processing core may generate the per application lean classifier model to include the features of interest.

Figure 6:
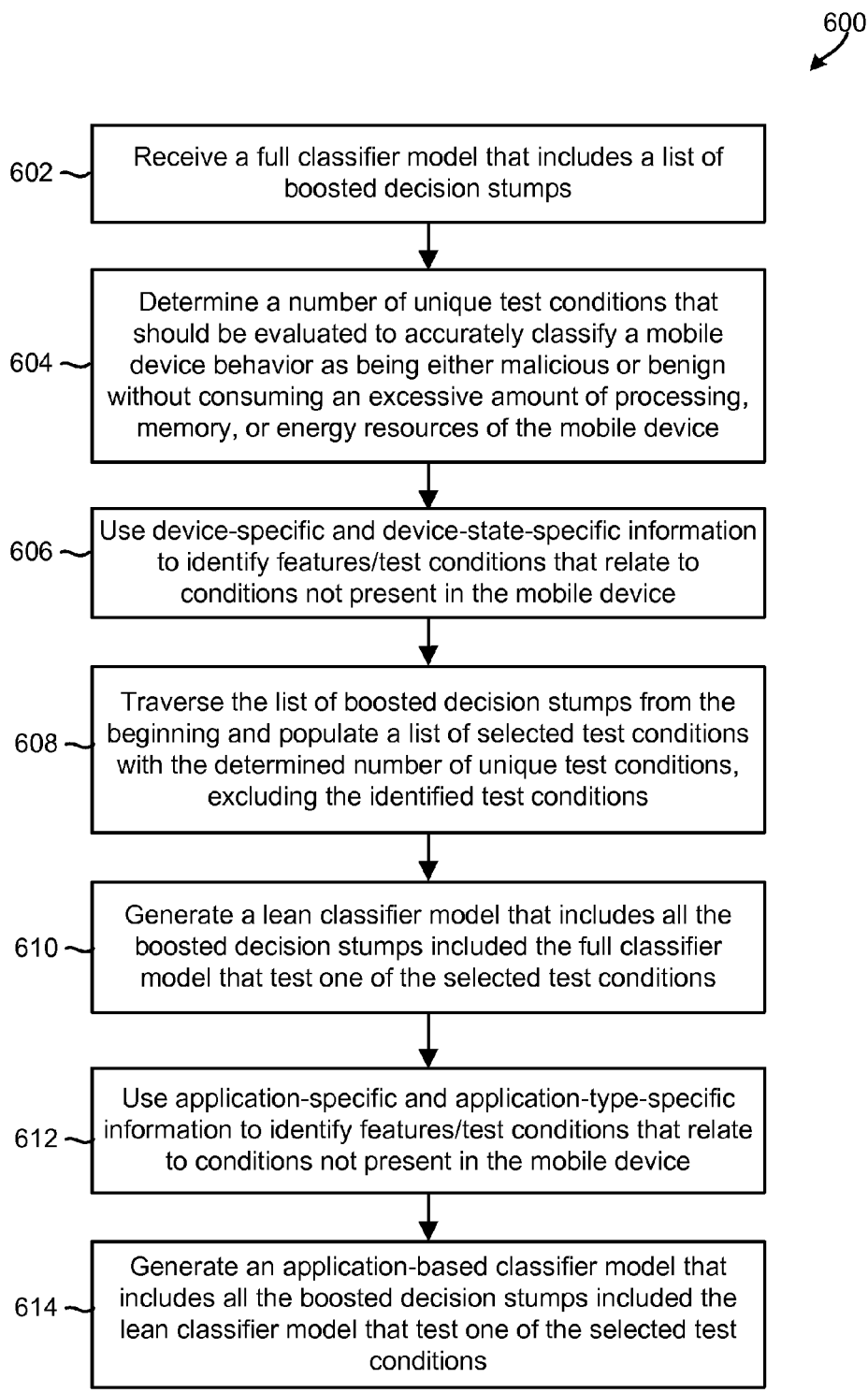
FIG. 6 is another process flow diagram illustrating another aspect mobile device method of generating application-based classifier models locally in the mobile device.

FIG. 6 illustrates an aspect method 600 of generating a lean or focused classifier/behavior models that account for application-specific and application-type-specific features of a mobile device.

In block 602 of method 600, the processing core may receive a full classifier model that is or includes a finite state machine, a list of boosted decision trees, stumps or other similar information structure that identifies a plurality of test conditions. In an aspect, the full classifier model includes a finite state machine that includes information suitable for expressing plurality of boosted decision stumps and/or which include information that is suitable for conversion by the mobile device into a plurality of boosted decision stumps. In an aspect, the finite state machine may be (or may include) an ordered or prioritized list of boosted decision stumps. Each of the boosted decision stumps may include a test condition and a weight value.

In block 604, the processing core may determine the number unique test conditions that should be evaluated to accurately classify a mobile device behavior as being either malicious or benign without consuming an excessive amount of processing, memory, or energy resources of the mobile device. This may include determining an amount of processing, memory, and/or energy resources available in the mobile device, the amount processing, memory, or energy resources of the mobile device that are required to test a condition, determining a priority and/or a complexity associated with a behavior or condition that is to be analyzed or evaluated in the mobile device by testing the condition, and selecting/determining the number of unique test conditions so as to strike a balance or tradeoff between the consumption of available processing, memory, or energy resources of the mobile device, the accuracy of the behavior classification that is to be achieved from testing the condition, and the importance or priority of the behavior that is tested by the condition.

In block 606, the processing core may use device-specific or device-state-specific information to quickly identify the features and/or test conditions that should be included or excluded from the lean classifier models. For example, the processing core may identify the test conditions that test conditions, features, or factors that cannot be present in the mobile device due to the mobile device's current hardware or software configuration, operating state, etc. As another example, the processing core may identify and exclude from the lean classifier models the features/nodes/stumps that are included in the full model and test conditions that cannot exist in the mobile device and/or which are not relevant to the mobile device.

In an aspect, in block 608, the processing core may traverse the list of boosted decision stumps from the beginning to populate a list of selected test conditions with the determined number of unique test conditions and to exclude the test conditions identified in block 606. For example, the processing core may skip, ignore, or delete features included in the full classifier model that test conditions that cannot be used by the software application. In an aspect, the processing core may also determine an absolute or relative priority value for each of the selected test conditions, and store the absolute or relative priorities value in association with their corresponding test conditions in the list of selected test conditions.

In an aspect, in block 608, the processing core may generating a list of test conditions by sequentially traversing the plurality of test conditions in the full classifier model and inserting those test conditions that are relevant to classifying the behavior of the mobile device into the list of test conditions until the list of test conditions includes the determined number of unique test conditions. In a further aspect, generating the list of test conditions may include sequentially traversing the decision nodes of the full classifier model, ignoring decision nodes associated with test conditions not relevant to the software application, and inserting test conditions associated with each sequentially traversed decision node that is not ignored into the list of test conditions until the list of test conditions includes the determined number of unique test conditions.

In block 610, the processing core may generate a lean classifier model that includes all the boosted decision stumps included in the full classifier model that test one of the selected test conditions (and thus exclude the test conditions identified in block 606) identified in the generated list of test conditions. In an aspect, the processing core may generate the lean classifier model to include or express the boosted decision stumps in order of their importance or priority value. In an aspect, in block 610, the processing core may increase the number of unique test conditions in order to generate another more robust (i.e., less lean) lean classifier model by repeating the operations of traversing the list of boosted decision stumps for a larger number test conditions in block 608 and generating another lean classifier mode. These operations may be repeated to generate a family of lean classifier models.

In block 612, the processing core may use application-specific information and/or application-type specific information to indentify features or test conditions that are included in the lean classifier model and which are relevant to determining whether a software application is contributing to a performance degrading behavior of a mobile device.

In block 614, the processing core may traverse the boosted decision stumps in the lean classifier model and select or map the decision stumps that test a feature or condition that is used by a software application to that software application, and use the selected or mapped decision stumps as an application-specific classifier model or an application-type-specific classifier model.

Figure 7:
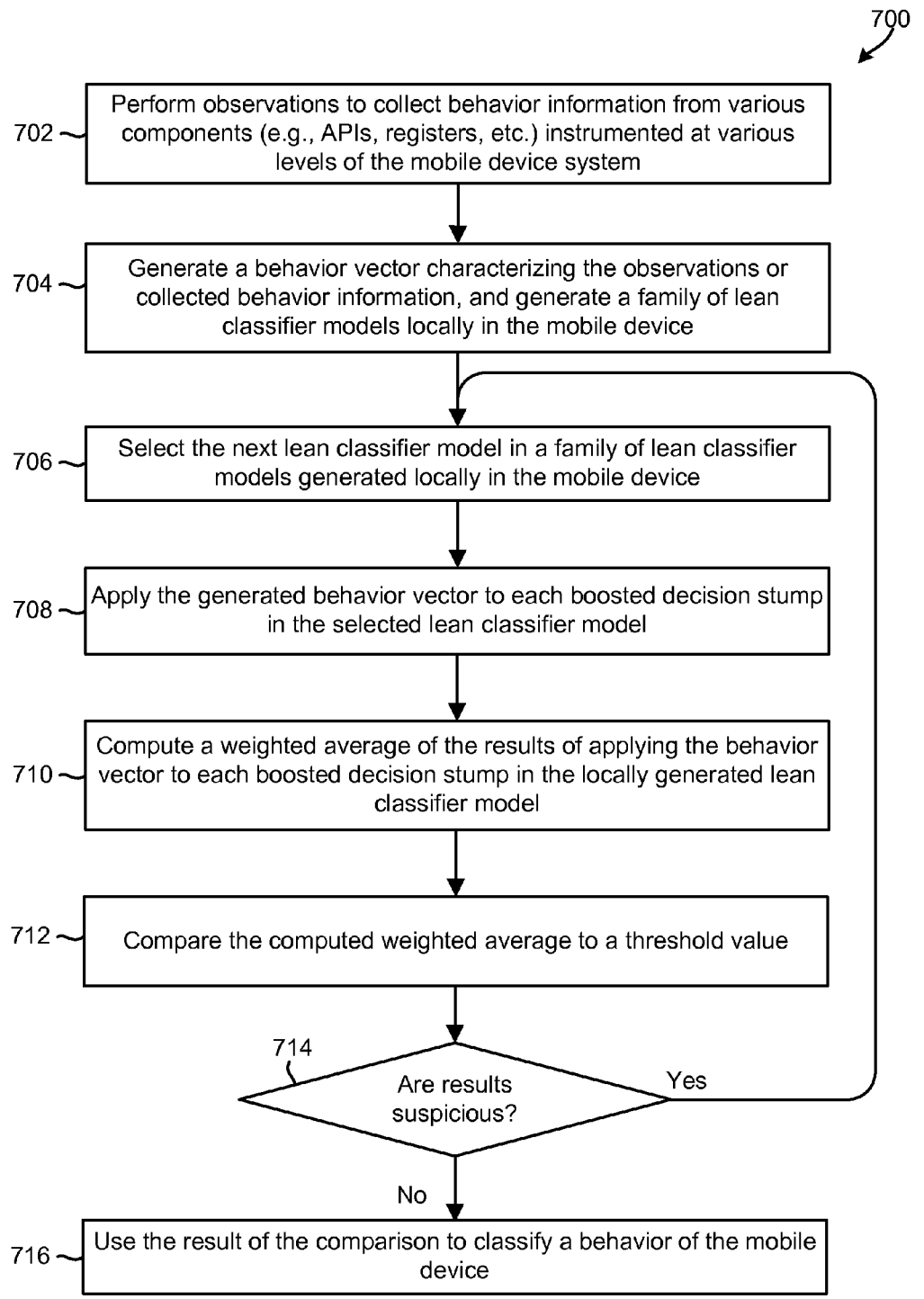
FIG. 7 is a process flow diagram illustrating another aspect mobile device method of generating an application-based or lean classifier models in the mobile device.

FIG. 7 illustrates an aspect method 700 of using a lean classifier model to classify a behavior of the mobile device. Method 700 may be performed by a processing core in a mobile device.

In block 702, the processing core my perform observations to collect behavior information from various components that are instrumented at various levels of the mobile device system. In an aspect, this may be accomplished via the behavior observer module 202 discussed above with reference to FIG. 2. In block 704, the processing core may generate a behavior vector characterizing the observations, the collected behavior information, and/or a mobile device behavior. Also in block 704, the processing core may use a full classifier model received from a network server to generate a lean classifier model or a family of lean classifier models of varying levels of complexity (or "leanness"). To accomplish this, the processing core may cull a family of boosted decision stumps included in the full classifier model to generate lean classifier models that include a reduced number of boosted decision stumps and/or evaluate a limited number of test conditions.

In block 706, the processing core may select the leanest classifier in the family of lean classifier models (i.e., the model based on the fewest number of different mobile device states, features, behaviors, or conditions) that has not yet been evaluated or applied by the mobile device. In an aspect, this may be accomplished by the processing core selecting the first classifier model in an ordered list of classifier models.

In block 708, the processing core may apply collected behavior information or behavior vectors to each boosted decision stump in the selected lean classifier model. Because boosted decision stumps are binary decisions and the lean classifier model is generated by selecting many binary decisions that are based on the same test condition, the process of applying a behavior vector to the boosted decision stumps in the lean classifier model may be performed in a parallel operation. Alternatively, the behavior vector applied in block 530 may be truncated or filtered to just include the limited number of test condition parameters included in the lean classifier model, thereby further reducing the computational effort in applying the model.

In block 710, the processing core may compute or determine a weighted average of the results of applying the collected behavior information to each boosted decision stump in the lean classifier model. In block 712, the processing core may compare the computed weighted average to a threshold value. In determination block 714, the processing core may determine whether the results of this comparison and/or the results generated by applying the selected lean classifier model are suspicious. For example, the processing core may determine whether these results may be used to classify a behavior as either malicious or benign with a high degree of confidence, and if not treat the behavior as suspicious.

If the processing core determines that the results are suspicious (e.g., determination block 714="Yes"), the processing core may repeat the operations in blocks 706-712 to select and apply a stronger (i.e., less lean) classifier model that evaluates more device states, features, behaviors, or conditions until the behavior is classified as malicious or benign with a high degree of confidence. If the processing core determines that the results are not suspicious (e.g., determination block 714="No"), such as by determining that the behavior can be classified as either malicious or benign with a high degree of confidence, in block 716, the processing core may use the result of the comparison generated in block 712 to classify a behavior of the mobile device as benign or potentially malicious.

In an alternative aspect method, the operations described above may be accomplished by sequentially selecting a boosted decision stump that is not already in the lean classifier model; identifying all other boosted decision stumps that depend upon the same mobile device state, feature, behavior, or condition as the selected decision stump (and thus can be applied based upon one determination result); including in the lean classifier model the selected and all identified other boosted decision stumps that that depend upon the same mobile device state, feature, behavior, or condition; and repeating the process for a number of times equal to the determined number of test conditions. Because all boosted decision stumps that depend on the same test condition as the selected boosted decision stump are added to the lean classifier model each time, limiting the number of times this process is performed will limit the number of test conditions included in the lean classifier model.

Figure 8:
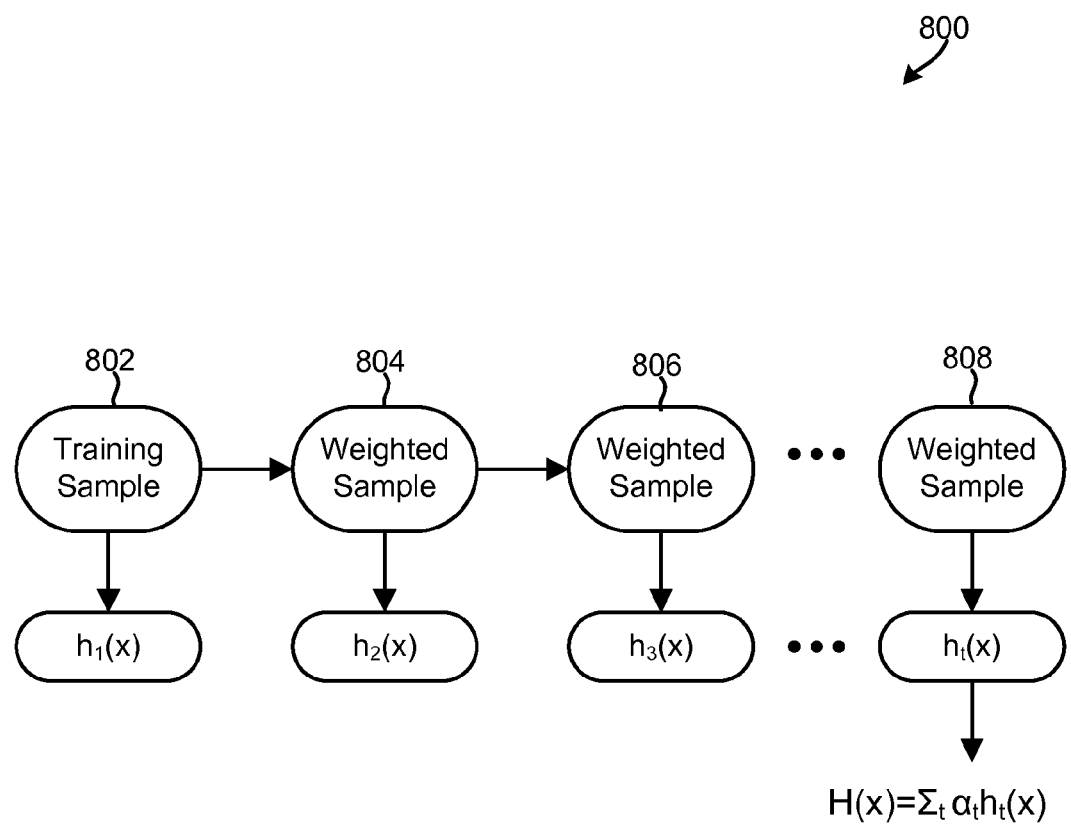
FIG. 8 is an illustration of example boosted decision stumps that may be generated by an aspect server processor and used by a mobile device processor to generate lean classifier models.

FIG. 8 illustrates an example boosting method 800 suitable for generating a boosted decision tree/classifier that is suitable for use in accordance with various aspects. In operation 802, a processor may generate and/or execute a decision tree/classifier, collect a training sample from the execution of the decision tree/classifier, and generate a new classifier model (h1(x)) based on the training sample. The training sample may include information collected from previous observations or analysis of mobile device behaviors, software applications, or processes in the mobile device. The training sample and/or new classifier model (h1(x)) may be generated based the types of question or test conditions included in previous classifiers and/or based on accuracy or performance characteristics collected from the execution/application of previous data/behavior models or classifiers in a classifier module 208 of a behavior analyzer module 204. In operation 804, the processor may boost (or increase) the weight of the entries that were misclassified by the generated decision tree/classifier (h1(x)) to generate a second new tree/classifier (h2(x)). In an aspect, the training sample and/or new classifier model (h2(x)) may be generated based on the mistake rate of a previous execution or use (h1(x)) of a classifier. In an aspect, the training sample and/or new classifier model (h2(x)) may be generated based on attributes determined to have that contributed to the mistake rate or the misclassification of data points in the previous execution or use of a classifier.

In an aspect, the misclassified entries may be weighted based on their relatively accuracy or effectiveness. In operation 806, the processor may boost (or increase) the weight of the entries that were misclassified by the generated second tree/classifier (h2(x)) to generate a third new tree/classifier (h3(x)). In operation 808, the operations of 804-806 may be repeated to generate "t" number of new tree/classifiers ($h_t(x)$).

By boosting or increasing the weight of the entries that were misclassified by the first decision tree/classifier (h1 (x)), the second tree/classifier (h2(x)) may more accurately classify the entities that were misclassified by the first decision tree/classifier (h1(x)), but may also misclassify some of the entities that where correctly classified by the first decision tree/classifier (h1(x)). Similarly, the third tree/classifier (h3(x)) may more accurately classify the entities that were misclassified by the second decision tree/classifier (h2(x)) and misclassify some of the entities that where correctly classified by the second decision tree/classifier (h2(x)). That is, generating the family of tree/classifiers h1(x)-$h_t(x)$ may not result in a system that converges as a whole, but results in a number of decision trees/classifiers that may be executed in parallel.

Figure 9:
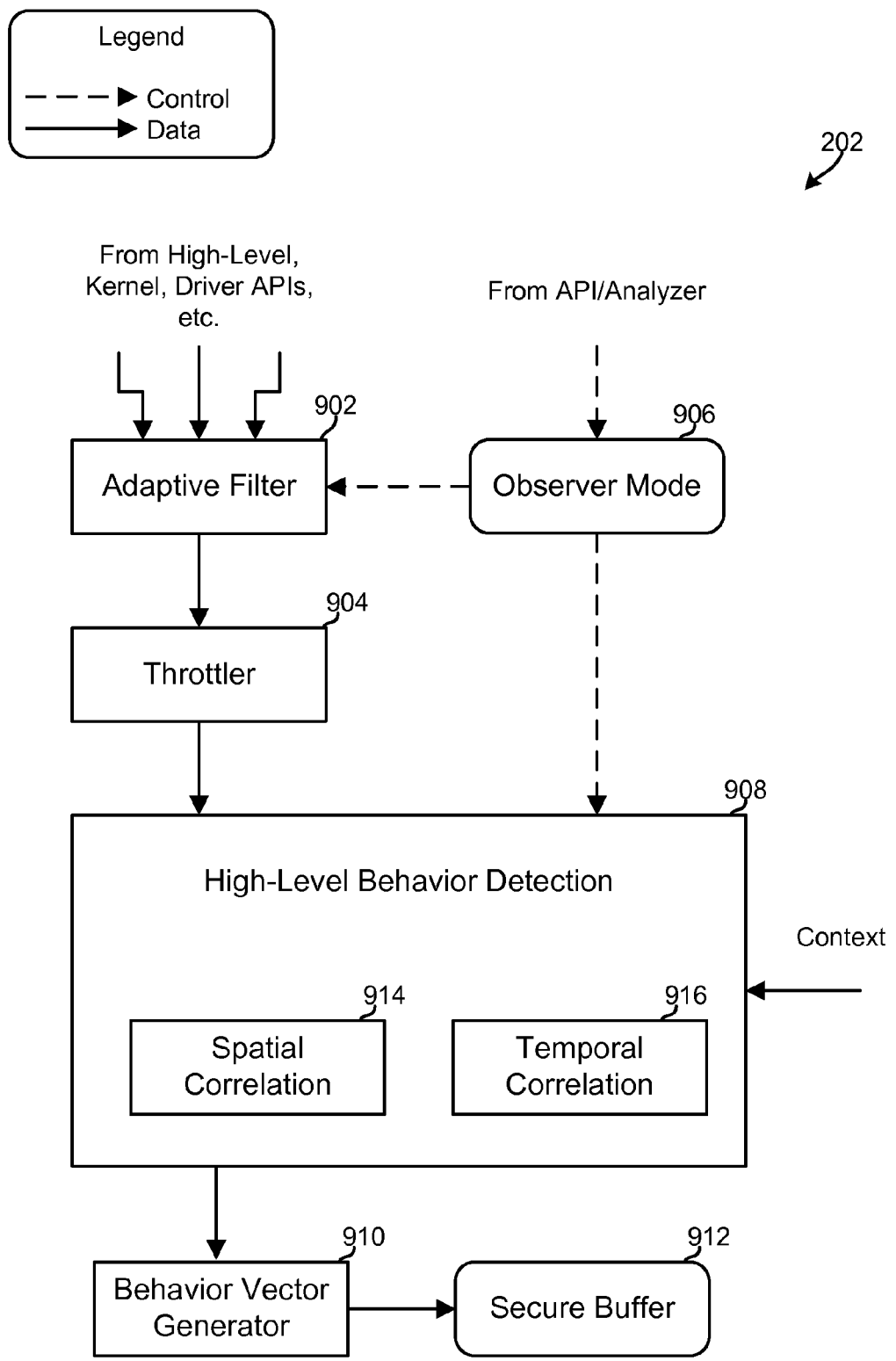
FIG. 9 is a block diagram illustrating example logical components and information flows in an observer module configured to perform dynamic and adaptive observations in accordance with an aspect.

FIG. 9 illustrates example logical components and information flows in a behavior observer module 202 of a computing system configured to perform dynamic and adaptive observations in accordance with an aspect. The behavior observer module 202 may include an adaptive filter module 902, a throttle module 904, an observer mode module 906, a high-level behavior detection module 908, a behavior vector generator 910, and a secure buffer 912. The high-level behavior detection module 908 may include a spatial correlation module 914 and a temporal correlation module 916.

The observer mode module 906 may receive control information from various sources, which may include an analyzer unit (e.g., the behavior analyzer module 204 described above with reference to FIG. 2) and/or an application API. The observer mode module 906 may send control information pertaining to various observer modes to the adaptive filter module 902 and the high-level behavior detection module 908.

The adaptive filter module 902 may receive data/information from multiple sources, and intelligently filter the received information to generate a smaller subset of information selected from the received information. This filter may be adapted based on information or control received from the analyzer module, or a higher-level process communicating through an API. The filtered information may be sent to the throttle module 904, which may be responsible for controlling the amount of information flowing from the filter to ensure that the high-level behavior detection module 908 does not become flooded or overloaded with requests or information.

The high-level behavior detection module 908 may receive data/information from the throttle module 904, control information from the observer mode module 906, and context information from other components of the mobile device. The high-level behavior detection module 908 may use the received information to perform spatial and temporal correlations to detect or identify high level behaviors that may cause the device to perform at sub-optimal levels. The results of the spatial and temporal correlations may be sent to the behavior vector generator 910, which may receive the correlation information and generate a behavior vector that describes the behaviors of a particular process, application, or sub-system. In an aspect, the behavior vector generator 910 may generate the behavior vector such that each high-level behavior of a particular process, application, or sub-system is an element of the behavior vector. In an aspect, the generated behavior vector may be stored in a secure buffer 912. Examples of high-level behavior detection may include detection of the existence of a particular event, the amount or frequency of another event, the relationship between multiple events, the order in which events occur, time differences between the occurrence of certain events, etc.

In the various aspects, the behavior observer module 202 may perform adaptive observations and control the observation granularity. That is, the behavior observer module 202 may dynamically identify the relevant behaviors that are to be observed, and dynamically determine the level of detail at which the identified behaviors are to be observed. In this manner, the behavior observer module 202 enables the system to monitor the behaviors of the mobile device at various levels (e.g., multiple coarse and fine levels). The behavior observer module 202 may enable the system to adapt to what is being observed. The behavior observer module 202 may enable the system to dynamically change the factors/behaviors being observed based on a focused subset of information, which may be obtained from a wide verity of sources.

As discussed above, the behavior observer module 202 may perform adaptive observation techniques and control the observation granularity based on information received from a variety of sources. For example, the high-level behavior detection module 908 may receive information from the throttle module 904, the observer mode module 906, and context information received from other components (e.g., sensors) of the mobile device. As an example, a high-level behavior detection module 908 performing temporal correlations might detect that a camera has been used and that the mobile device is attempting to upload the picture to a server. The high-level behavior detection module 908 may also perform spatial correlations to determine whether an application on the mobile device took the picture while the device was holstered and attached to the user's belt. The high-level behavior detection module 908 may determine whether this detected high-level behavior (e.g., usage of the camera while holstered) is a behavior that is acceptable or common, which may be achieved by comparing the current behavior with past behaviors of the mobile device and/or accessing information collected from a plurality of devices (e.g., information received from a crowd-sourcing server). Since taking pictures and uploading them to a server while holstered is an unusual behavior (as may be determined from observed normal behaviors in the context of being holstered), in this situation the high-level behavior detection module 908 may recognize this as a potentially threatening behavior and initiate an appropriate response (e.g., shutting off the camera, sounding an alarm, etc.).

In an aspect, the behavior observer module 202 may be implemented in multiple parts.

Figure 10:
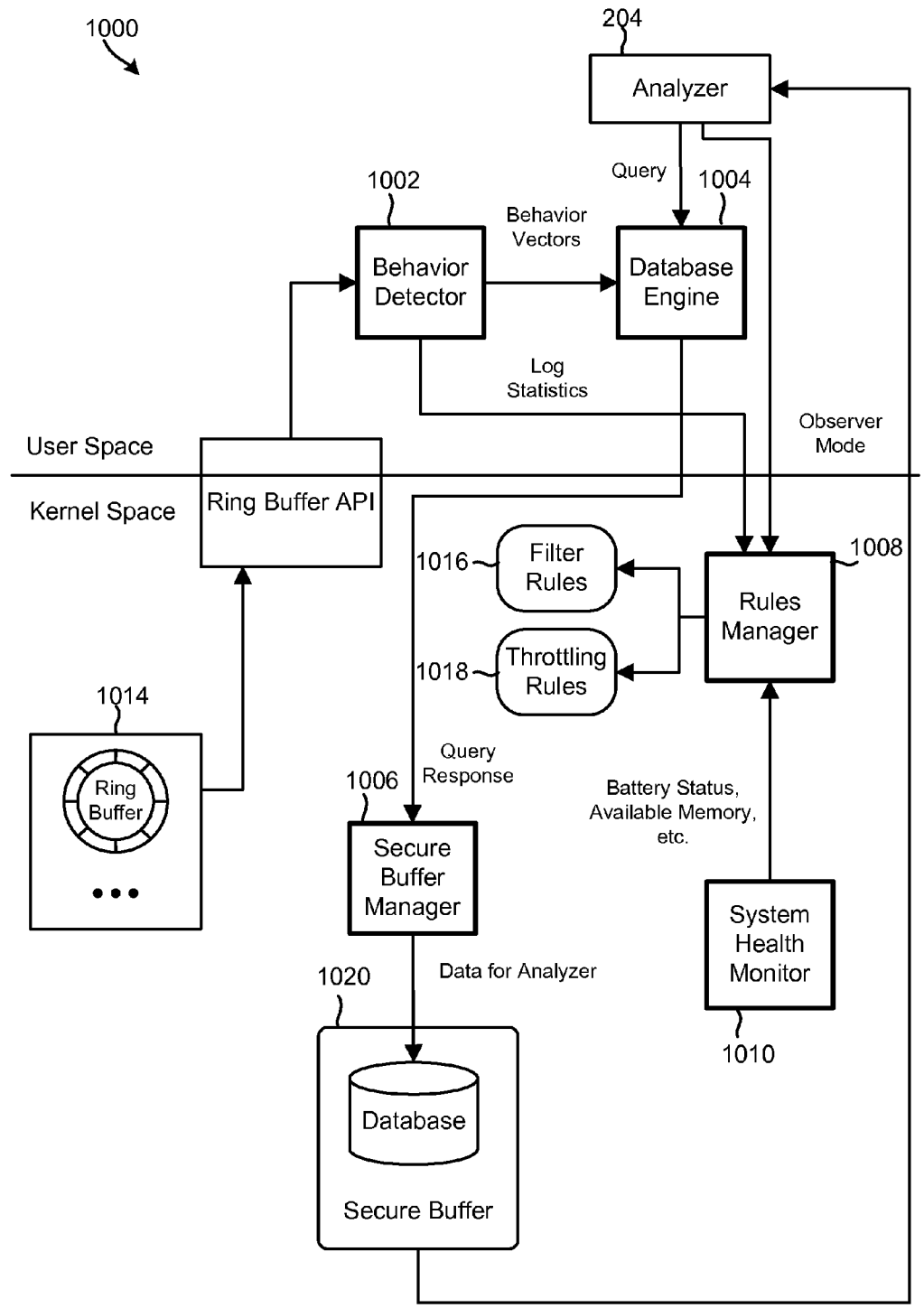
FIG. 10 is a block diagram illustrating logical components and information flows in a computing system implementing observer daemons in accordance with another aspect.

FIG. 10 illustrates in more detail logical components and information flows in a computing system 1000 implementing an aspect observer daemon. In the example illustrated in FIG. 10, the computing system 1000 includes a behavior detector 1002 module, a database engine 1004 module, and a behavior analyzer module 204 in the user space, and a ring buffer 1014, a filter rules 1016 module, a throttling rules 1018 module, and a secure buffer 1020 in the kernel space. The computing system 1000 may further include an observer daemon that includes the behavior detector 1002 and the database engine 1004 in the user space, and the secure buffer manager 1006, the rules manager 1008, and the system health monitor 1010 in the kernel space.

The various aspects may provide cross-layer observations on mobile devices encompassing webkit, SDK, NDK, kernel, drivers, and hardware in order to characterize system behavior. The behavior observations may be made in real time.

The observer module may perform adaptive observation techniques and control the observation granularity. As discussed above, there are a large number (i.e., thousands) of factors that could contribute to the mobile device's degradation, and it may not be feasible to monitor/observe all of the different factors that may contribute to the degradation of the device's performance. To overcome this, the various aspects dynamically identify the relevant behaviors that are to be observed, and dynamically determine the level of detail at which the identified behaviors are to be observed.

Figure 11:
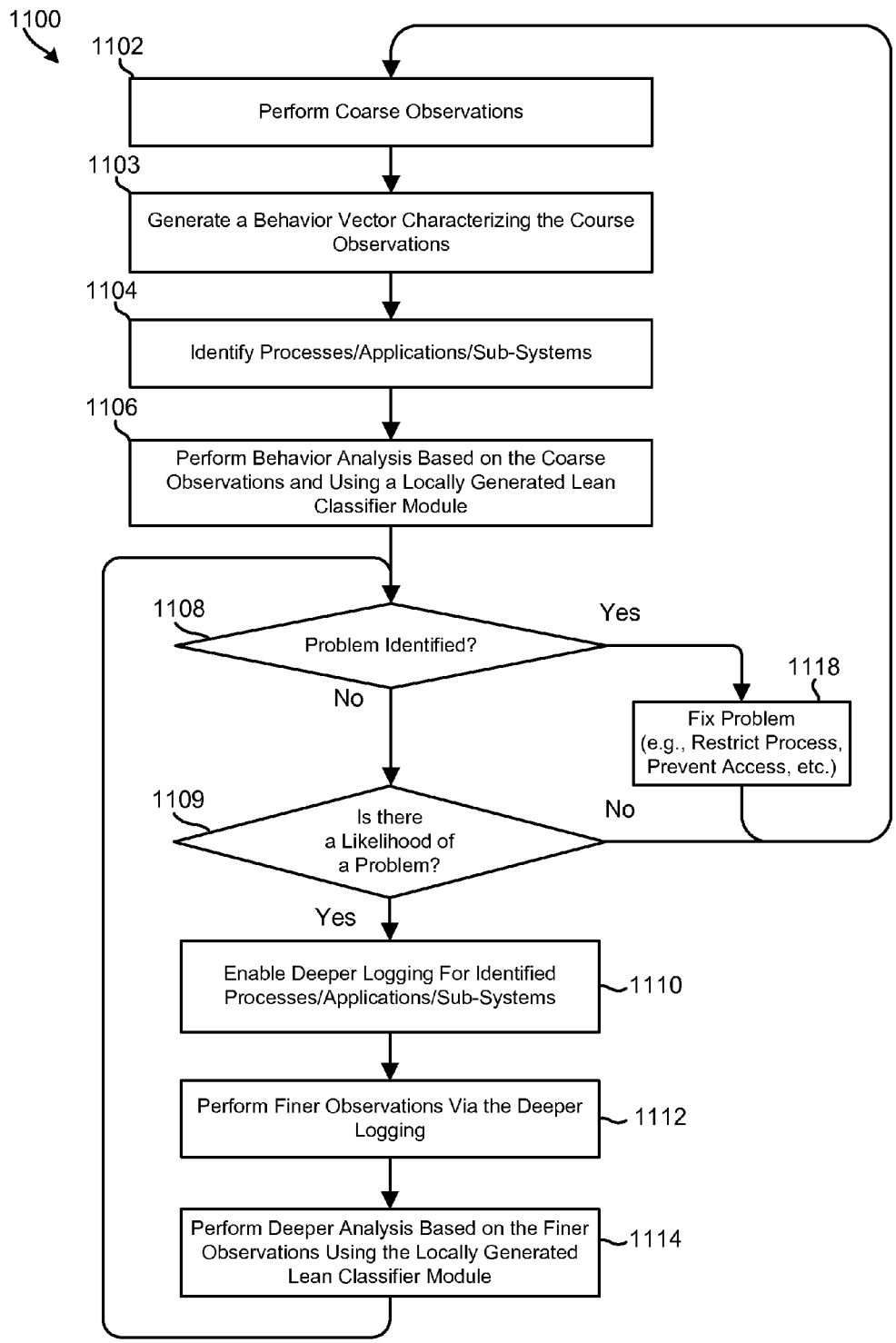
FIG. 11 is a process flow diagram illustrating an aspect method for performing adaptive observations on mobile devices.

FIG. 11 illustrates an example method 1100 for performing dynamic and adaptive observations in accordance with an aspect. In block 1102, the mobile device processor may perform coarse observations by monitoring/observing a subset of a large number factors/behaviors that could contribute to the mobile device's degradation. In block 1103, the mobile device processor may generate a behavior vector characterizing the coarse observations and/or the mobile device behavior based on the coarse observations. In block 1104, the mobile device processor may identify subsystems, processes, and/or applications associated with the coarse observations that may potentially contribute to the mobile device's degradation. This may be achieved, for example, by comparing information received from multiple sources with contextual information received from sensors of the mobile device. In block 1106, the mobile device processor may perform behavioral analysis operations based on the coarse observations. In an aspect, as part of blocks 1103 and 1104, the mobile device processor may perform one or more of the operations discussed above with reference to FIGS. 2-10.

In determination block 1108, the mobile device processor may determine whether suspicious behaviors or potential problems can be identified and corrected based on the results of the behavioral analysis. When the mobile device processor determines that the suspicious behaviors or potential problems can be identified and corrected based on the results of the behavioral analysis (i.e., determination block 1108="Yes"), in block 1118, the processor may initiate a process to correct the behavior and return to block 1102 to perform additional coarse observations.

When the mobile device processor determines that the suspicious behaviors or potential problems cannot be identified and/or corrected based on the results of the behavioral analysis (i.e., determination block 1108="No"), in determination block 1109 the mobile device processor may determine whether there is a likelihood of a problem. In an aspect, the mobile device processor may determine that there is a likelihood of a problem by computing a probability of the mobile device encountering potential problems and/or engaging in suspicious behaviors, and determining whether the computed probability is greater than a predetermined threshold. When the mobile device processor determines that the computed probability is not greater than the predetermined threshold and/or there is not a likelihood that suspicious behaviors or potential problems exist and/or are detectable (i.e., determination block 1109="No"), the processor may return to block 1102 to perform additional coarse observations.

When the mobile device processor determines that there is a likelihood that suspicious behaviors or potential problems exist and/or are detectable (i.e., determination block 1109="Yes"), in block 1110, the mobile device processor may perform deeper logging/observations or final logging on the identified subsystems, processes or applications. In block 1112, the mobile device processor may perform deeper and more detailed observations on the identified subsystems, processes or applications. In block 1114, the mobile device processor may perform further and/or deeper behavioral analysis based on the deeper and more detailed observations. In determination block 1108, the mobile device processor may again determine whether the suspicious behaviors or potential problems can be identified and corrected based on the results of the deeper behavioral analysis. When the mobile device processor determines that the suspicious behaviors or potential problems cannot be identified and corrected based on the results of the deeper behavioral analysis (i.e., determination block 1108="No"), the processor may repeat the operations in blocks 1110-1114 until the level of detail is fine enough to identify the problem or until it is determined that the problem cannot be identified with additional detail or that no problem exists.

When the mobile device processor determines that the suspicious behaviors or potential problems can be identified and corrected based on the results of the deeper behavioral analysis (i.e., determination block 1108="Yes"), in block 1118, the mobile device processor may perform operations to correct the problem/behavior, and the processor may return to block 1102 to perform additional operations.

In an aspect, as part of blocks 1102-1118 of method 1100, the mobile device processor may perform real-time behavior analysis of the system's behaviors to identify suspicious behaviors from limited and coarse observations, to dynamically determine the behaviors to observe in greater detail, and to dynamically determine the precise level of detail required for the observations. This enables the mobile device processor to efficiently identify and prevent problems from occurring, without requiring the use of a large amount of processor, memory, or battery resources on the device.

Figure 12:
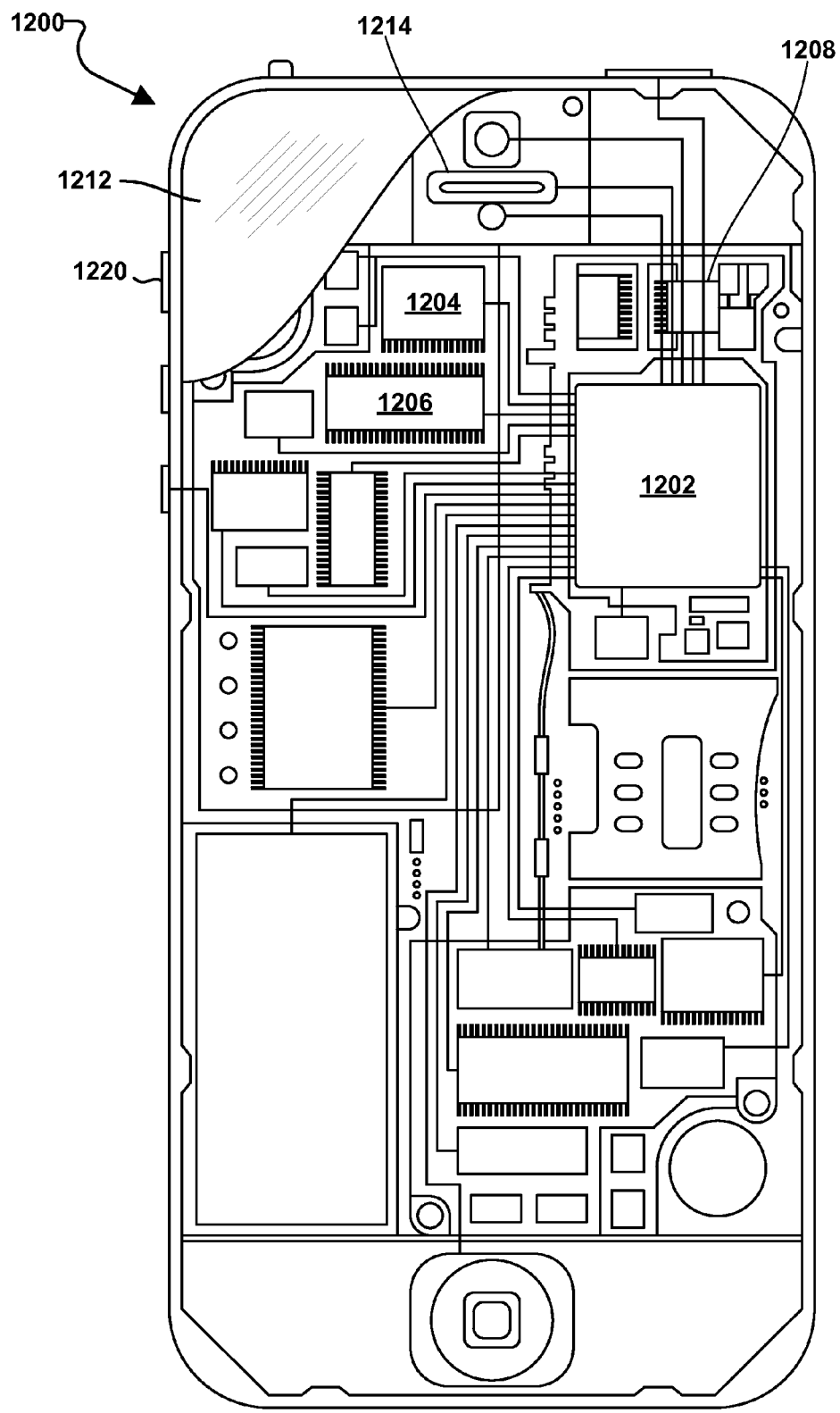
FIG. 12 is a component block diagram of a mobile device suitable for use in an aspect.

The various aspects may be implemented on a variety of computing devices, an example of which is illustrated in FIG. 12 in the form of a smartphone. A smartphone 1200 may include a processor 1202 coupled to internal memory 1204, a display 1212, and to a speaker 1214. Additionally, the smartphone 1200 may include an antenna for sending and receiving electromagnetic radiation that may be connected to a wireless data link and/or cellular telephone transceiver 1208 coupled to the processor 1202. Smartphones 1200 typically also include menu selection buttons or rocker switches 1220 for receiving user inputs.

A typical smartphone 1200 also includes a sound encoding/decoding (CODEC) circuit 1206, which digitizes sound received from a microphone into data packets suitable for wireless transmission and decodes received sound data packets to generate analog signals that are provided to the speaker to generate sound. Also, one or more of the processor 1202, wireless transceiver 1208 and CODEC 1206 may include a digital signal processor (DSP) circuit (not shown separately).

Figure 13:
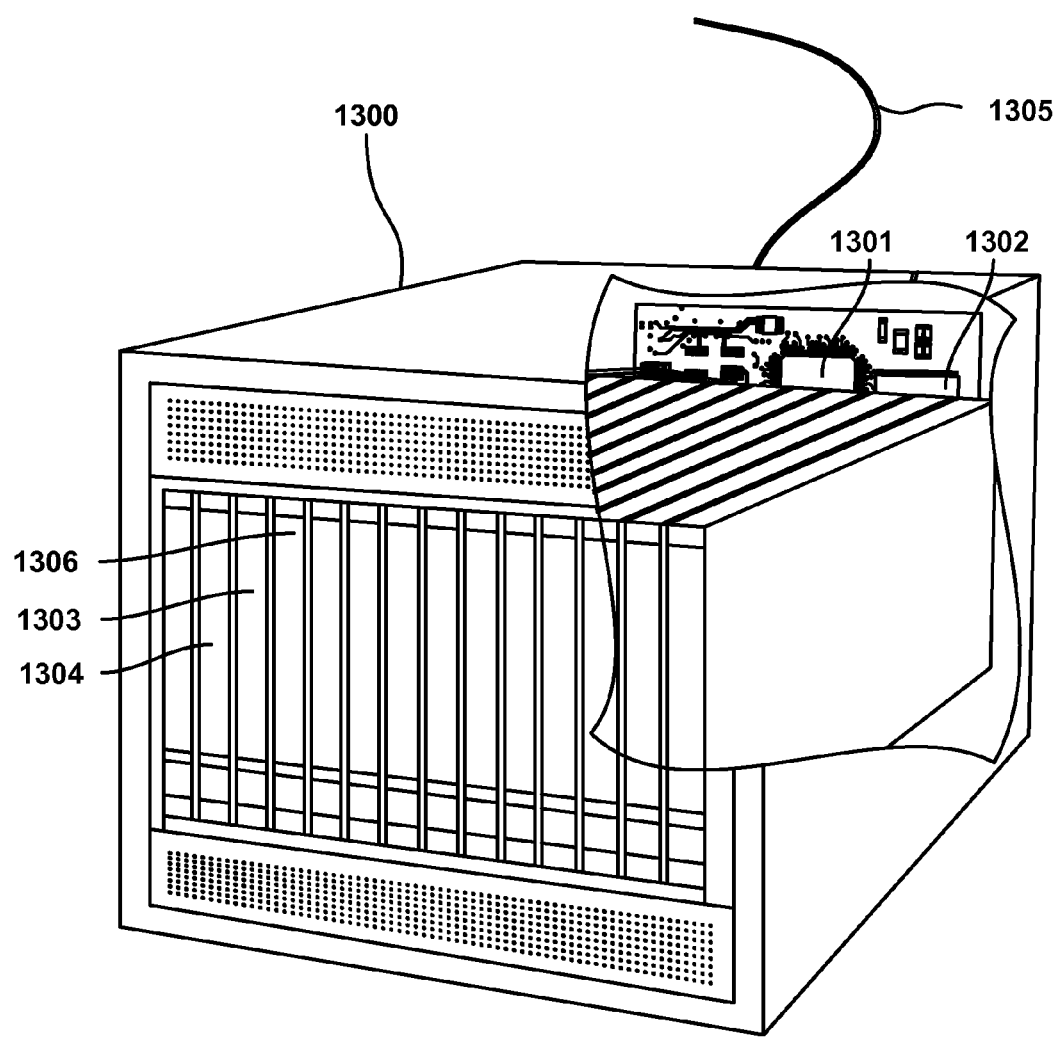
FIG. 13 is a component block diagram of a server device suitable for use in an aspect.

Portions of the aspect methods may be accomplished in a client-server architecture with some of the processing occurring in a server, such as maintaining databases of normal operational behaviors, which may be accessed by a mobile device processor while executing the aspect methods. Such aspects may be implemented on any of a variety of commercially available server devices, such as the server 1300 illustrated in FIG. 13. Such a server 1300 typically includes a processor 1301 coupled to volatile memory 1302 and a large capacity nonvolatile memory, such as a disk drive 1303. The server 1300 may also include a floppy disc drive, compact disc (CD) or DVD disc drive 1304 coupled to the processor 1301. The server 1300 may also include network access ports 1306 coupled to the processor 1301 for establishing data connections with a network 1305, such as a local area network coupled to other broadcast system computers and servers.

The processors 1202, 1301 may be any programmable microprocessor, microcomputer or multiple processor chip or chips that can be configured by software instructions (applications) to perform a variety of functions, including the functions of the various aspects described below. In some mobile devices, multiple processors 1202 may be provided, such as one processor dedicated to wireless communication functions and one processor dedicated to running other applications. Typically, software applications may be stored in the internal memory 1204, 1302, 1303 before they are accessed and loaded into the processor 1202, 1301. The processor 1202, 1301 may include internal memory sufficient to store the application software instructions.

A number of different cellular and mobile communication services and standards are available or contemplated in the future, all of which may implement and benefit from the various aspects. Such services and standards include, e.g., third generation partnership project (3GPP), long term evolution (LTE) systems, third generation wireless mobile communication technology (3G), fourth generation wireless mobile communication technology (4G), global system for mobile communications (GSM), universal mobile telecommunications system (UMTS), 3GSM, general packet radio service (GPRS), code division multiple access (CDMA) systems (e.g., cdmaOne, CDMA1020™), enhanced data rates for GSM evolution (EDGE), advanced mobile phone system (AMPS), digital AMPS (IS-136/TDMA), evolution-data optimized (EV-DO), digital enhanced cordless telecommunications (DECT), Worldwide Interoperability for Microwave Access (WiMAX), wireless local area network (WLAN), Wi-Fi Protected Access I & II (WPA, WPA2), and integrated digital enhanced network (iden). Each of these technologies involves, for example, the transmission and reception of voice, data, signaling, and/or content messages. It should be understood that any references to terminology and/or technical details related to an individual telecommunication standard or technology are for illustrative purposes only, and are not intended to limit the scope of the claims to a particular communication system or technology unless specifically recited in the claim language.

The term "performance degradation" is used in this application to refer to a wide variety of undesirable mobile device operations and characteristics, such as longer processing times, slower real time responsiveness, lower battery life, loss of private data, malicious economic activity (e.g., sending unauthorized premium SMS message), denial of service (DoS), operations relating to commandeering the mobile device or utilizing the phone for spying or botnet activities, etc.

Computer program code or "program code" for execution on a programmable processor for carrying out operations of the various aspects may be written in a high level programming language such as C, C++, C#, Smalltalk, Java, JavaScript, Visual Basic, a Structured Query Language (e.g., Transact-SQL), Perl, or in various other programming languages. Program code or programs stored on a computer readable storage medium as used in this application may refer to machine language code (such as object code) whose format is understandable by a processor.

Many mobile computing devices operating system kernels are organized into a user space (where non-privileged code runs) and a kernel space (where privileged code runs). This separation is of particular importance in Android® and other general public license (GPL) environments where code that is part of the kernel space must be GPL licensed, while code running in the user-space may not be GPL licensed. It should be understood that the various software components/modules discussed here may be implemented in either the kernel space or the user space, unless expressly stated otherwise.

The foregoing method descriptions and the process flow diagrams are provided merely as illustrative examples, and are not intended to require or imply that the steps of the various aspects must be performed in the order presented. As will be appreciated by one of skill in the art the order of steps in the foregoing aspects may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

As used in this application, the terms "component," "module," "system," "engine," "generator," "manager," and the like are intended to include a computer-related entity, such as, but not limited to, hardware, firmware, a combination of hardware and software, software, or software in execution, which are configured to perform particular operations or functions. For example, a component may be, but is not limited to, a process running on a processor, a processor, an object, an executable, a thread of execution, a program, and/or a computer. By way of illustration, both an application running on a computing device and the computing device may be referred to as a component. One or more components may reside within a process and/or thread of execution, and a component may be localized on one processor or core and/or distributed between two or more processors or cores. In addition, these components may execute from various non-transitory computer readable media having various instructions and/or data structures stored thereon. Components may communicate by way of local and/or remote processes, function or procedure calls, electronic signals, data packets, memory read/writes, and other known network, computer, processor, and/or process related communication methodologies.

The various illustrative logical blocks, modules, circuits, and algorithm steps described in connection with the aspects disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a multiprocessor, but, in the alternative, the processor may be any conventional processor, controller, microcontroller, or state machine. A processor may also be implemented as a combination of computing devices, e.g., a combination of a DSP and a multiprocessor, a plurality of multiprocessors, one or more multiprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more processor-executable instructions or code on a non-transitory computer-readable storage medium or non-transitory processor-readable storage medium. The steps of a method or algorithm disclosed herein may be embodied in a processor-executable software module which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed aspects is provided to enable any person skilled in the art to make or use the present invention. Various modifications to these aspects will be readily apparent to those skilled in the art, and the generic principles defined herein may be applied to other aspects without departing from the spirit or scope of the invention. Thus, the present invention is not intended to be limited to the aspects shown herein but is to be accorded the widest scope consistent with the following claims and the principles and novel features disclosed herein.

What is claimed is:

1. A method of generating and using classifier models in a mobile device based on application types having distinct characteristics, comprising:
   receiving, in a processor of the mobile device, a finite state machine that includes information that is suitable for conversion into a plurality of boosted decision stumps, wherein each of the plurality of boosted decision stumps evaluate one of a plurality of test conditions;
   converting the information included in the received finite state machine into the plurality of boosted decision stumps that each evaluate one of the plurality of test conditions;
   generating a family of lean classifier models in the mobile device based on the plurality of boosted decision stumps;
   generating, via the processor of the mobile device, an application-type-specific classifier model that includes and prioritizes boosted decision stumps in the plurality of boosted decision stumps that evaluate a subset of test conditions in the plurality of test conditions, wherein the subset of test conditions are determined to evaluate mobile device features that are used by one type of software application, wherein the one type of software application is determined to be suitable for executing on the mobile device;

selecting a lean classifier model from the family of lean classifier models; and applying collected behavior information to the generated application-type-specific classifier model and the selected lean classifier model in parallel to classify a behavior of the mobile device.

2. The method of claim 1, further comprising:

monitoring the behavior over a period of time by collecting behavior information from a mobile device component, wherein applying the collected behavior information to the generated application-type-specific classifier model and the selected lean classifier model in parallel to classify the behavior of the mobile device comprises:

using the behavior information to generate a feature vector;

evaluating each test condition included in the application-type-specific classifier model by applying the generated feature vector to the application-type-specific classifier model;

computing a weighted average of each result of evaluating test conditions in the application-type-specific classifier model; and determining whether the behavior is benign based on the computed weighted average.

3. The method of claim 1, wherein generating the application-type-specific classifier model further comprises:

determining a number of unique test conditions that should be evaluated to classify the behavior without consuming an excessive amount of mobile device resources.

4. The method of claim 1, further comprising:

monitoring a software application to detect a change in one of:
a state of the software application,
a configuration of the software application,
an operation of the software application, and
a functionality of the software application.

5. The method of claim 4, further comprising:

identifying a feature associated with the detected change;

determining whether the identified feature is included in the application-type-specific classifier model; and identifying a test condition in the plurality of test conditions that evaluate the identified feature and adding the identified test condition to the application-type-specific classifier model in response to determining that the identified feature is not included in the application-type-specific classifier model.

6. The method of claim 1, further comprising generating the finite state machine in a server by:

receiving in the server a corpus of behavior information;

generating the finite state machine based on the corpus of behavior information; and sending the finite state machine to the mobile device.

7. A mobile computing device, comprising:

a memory; and a processor coupled to the memory, wherein the processor is configured with processor-executable instructions to perform operations comprising:

receiving a finite state machine that includes information that is suitable for conversion into a plurality of boosted decision stumps, wherein each of the plurality of boosted decision stumps evaluate one of a plurality of test conditions;

converting the information included in the received finite state machine into the plurality of boosted decision stumps that each evaluate one of the plurality of test conditions;

generating a family of lean classifier models based on the plurality of boosted decision stumps;

generating an application-type-specific classifier model that includes and prioritizes boosted decision stumps in the plurality of boosted decision stumps that evaluate a subset of test conditions in the plurality of test conditions, wherein the subset of test conditions are determined to evaluate mobile device features that are used by one type of software application, wherein the one type of software application is determined to be suitable for executing on the mobile device;

selecting a lean classifier model from the family of lean classifier models; and applying collected behavior information to the generated application-type-specific classifier model and the selected lean classifier model in parallel to classify a behavior of the mobile computing device.

8. The mobile computing device of claim 7, wherein:

the processor is configured with processor-executable instructions to perform operations further comprising monitoring the behavior over a period of time by collecting behavior information from a mobile device component; and the processor is configured with processor-executable instructions to perform operations such that applying collected behavior information to the generated application-type-specific classifier model and the selected lean classifier model in parallel to classify the behavior comprises:

using the behavior information to generate a feature vector;

evaluating each test condition included in the application-type-specific classifier model by applying the generated feature vector to the application-type-specific classifier model;

computing a weighted average of each result of evaluating test conditions in the application-type-specific classifier model; and determining whether the behavior is benign based on the computed weighted average.

9. The mobile computing device of claim 7, wherein the processor is configured with processor-executable instructions to perform operations such that generating the application-type-specific classifier model comprises:

determining a number of unique test conditions that should be evaluated to classify the behavior without consuming an excessive amount of mobile device resources.

10. A non-transitory computer readable storage medium having stored thereon processor-executable software instructions configured to cause a processor of a mobile device to perform operations comprising:

receiving a finite state machine that includes information that is suitable for conversion into a plurality of boosted decision stumps, wherein each of the plurality of boosted decision stumps evaluate one of a plurality of test conditions;

converting the information included in the received finite state machine into the plurality of boosted decision stumps that each evaluate one of the plurality of test conditions;

generating a family of lean classifier models in the mobile device based on the plurality of boosted decision stumps;

generating an application-type-specific classifier model that includes and prioritizes boosted decision stumps in the plurality of boosted decision stumps that evaluate a subset of test conditions in the plurality of test conditions, wherein the subset of test conditions are determined to evaluate mobile device features that are used by one type of software application wherein the one type of software application is determined to be suitable for executing on the mobile device;

selecting a lean classifier model from the family of lean classifier models; and applying collected behavior information to the generated application-type-specific classifier model and the selected lean classifier model in parallel to classify a behavior of the mobile device.

11. The non-transitory computer readable storage medium of claim 10, wherein:

the stored processor-executable software instructions are configured to cause a processor to perform operations further comprising monitoring the behavior over a period of time by collecting behavior information from a mobile device component; and the stored processor-executable software instructions are configured to cause a processor to perform operations such that applying collected behavior information to the generated application-type-specific classifier model and the selected lean classifier model in parallel to classify the behavior of the mobile device comprises:

using the behavior information to generate a feature vector;

evaluating each test condition included in the application-type-specific classifier model by applying the generated feature vector to the application-type-specific classifier model;

computing a weighted average of each result of evaluating test conditions in the application-type-specific classifier model; and determining whether the behavior is benign based on the computed weighted average.

12. The non-transitory computer readable storage medium of claim 10, wherein the stored processor-executable software instructions are configured to cause a processor to perform operations such that generating the application-type-specific classifier model further comprises:

determining a number of unique test conditions that should be evaluated to classify the behavior without consuming an excessive amount of mobile device resources.

13. A mobile computing device, comprising:

means for receiving a finite state machine that includes information that is suitable for conversion into a plurality of boosted decision stumps, wherein each of the plurality of boosted decision stumps evaluate one of a plurality of test conditions;

means for converting the information included in the received finite state machine into the plurality of boosted decision stumps that each evaluate one of the plurality of test conditions;

means for generating a family of lean classifier models based on the plurality of boosted decision stumps;

means for generating an application-type-specific classifier model that includes and prioritizes boosted decision stumps in the plurality of boosted decision stumps that evaluate a subset of test conditions in the plurality of test conditions, wherein the subset of test conditions are determined to evaluate mobile device features that are used by one type of software application, wherein the one type of software application is determined to be suitable for executing on the mobile device;

means for selecting a lean classifier model from the family of lean classifier models; and means for applying collected behavior information to the generated application-type-specific classifier model and the selected lean classifier model in parallel to classify a behavior of the mobile computing device.

14. The mobile computing device of claim 13, further comprising:

means for monitoring the behavior over a period of time by collecting behavior information from a mobile device component, wherein means for applying collected behavior information to the generated application-type-specific classifier model and the selected lean classifier model in parallel to classify the behavior of the mobile computing device comprises:

means for using the behavior information to generate a feature vector;

means for evaluating each test condition included in the application-type-specific classifier model by applying the generated feature vector to the application-type-specific classifier model;

means for computing a weighted average of each result of evaluating test conditions in the application-type-specific classifier model; and means for determining whether the behavior is benign based on the computed weighted average.

15. The mobile computing device of claim 13, wherein means for generating the application-type-specific classifier model further comprises:

means for determining a number of unique test conditions that should be evaluated to classify the behavior without consuming an excessive amount of mobile device resources.

16. The mobile computing device of claim 13, further comprising:

means for monitoring a software application to detect a change in one of: a state of the software application, a configuration of the software application, an operation of the software application, and a functionality of the software application.

* * * * *